(12) United States Patent  
Saadat et al.

(10) Patent No.: US 8,628,541 B2  
(45) Date of Patent: Jan. 14, 2014

(54) METHODS AND APPARATUS FOR SECURING AND DEPLOYING TISSUE ANCHORS

(75) Inventors: Vahid Saadat, Saratoga, CA (US); Richard C. Ewers, Fullerton, CA (US); Cang C. Lam, Irvine, CA (US)

(73) Assignee: USGI Medical, Inc., San Clemente, CA (US)

( * ) Notice: Subject to any disclaimer, the term of this patent is extended or adjusted under 35 U.S.C. 154(b) by 2662 days.

(21) Appl. No.: 11/238,543

(22) Filed: Sep. 30, 2005

(65) Prior Publication Data

US 2006/0271101 A1 Nov. 30, 2006

Related U.S. Application Data

(63) Continuation-in-part of application No. 11/139,920, filed on May 26, 2005.

(51) Int. Cl.  
*A61B 17/10* (2006.01)

(52) U.S. Cl.  
USPC .......................................................... 606/139

(58) Field of Classification Search  
USPC .......................................... 606/139, 144–150  
See application file for complete search history.

(56) References Cited

U.S. PATENT DOCUMENTS

| | | | |
|---|---|---|---|
| 4,235,238 A * | 11/1980 | Ogiu et al. | 606/145 |
| 5,403,326 A | 4/1995 | Harrison et al. | |
| 6,592,596 B1 | 7/2003 | Geitz | |
| 7,347,863 B2 | 3/2008 | Rothe et al. | |
| 7,618,426 B2 * | 11/2009 | Ewers et al. | 606/139 |
| 2003/0130561 A1* | 7/2003 | Suzuki et al. | 600/107 |
| 2003/0236535 A1* | 12/2003 | Onuki et al. | 606/144 |
| 2004/0162568 A1 | 8/2004 | Saadat et al. | |
| 2004/0225183 A1 | 11/2004 | Michlitsch et al. | |
| 2005/0251157 A1 | 11/2005 | Saadat et al. | |

* cited by examiner

*Primary Examiner* — Gregory Anderson  
(74) *Attorney, Agent, or Firm* — Kenneth H. Ohriner; Perkins Coie LLP

(57) ABSTRACT

Methods and apparatus for securing and deploying tissue anchors are described herein. A tissue manipulation assembly is pivotably coupled to the distal end of a tubular member. A reconfigurable launch tube is also pivotably coupled to the tissue manipulation assembly, which may be advanced through a shape-lockable endoscopic device, a conventional endoscope, or directly by itself into a patient. A second tool can be used in combination with the tissue manipulation assembly to engage tissue and manipulate the tissue in conjunction with the tissue manipulation assembly. A deployment assembly is provided for securing engaged tissue via one or more tissue anchors, the deployment assembly also being configured to disengage the anchors endoluminally or laparoscopically by applying thermal energy through at least one suture cutting element disposed along the deployment assembly.

15 Claims, 30 Drawing Sheets

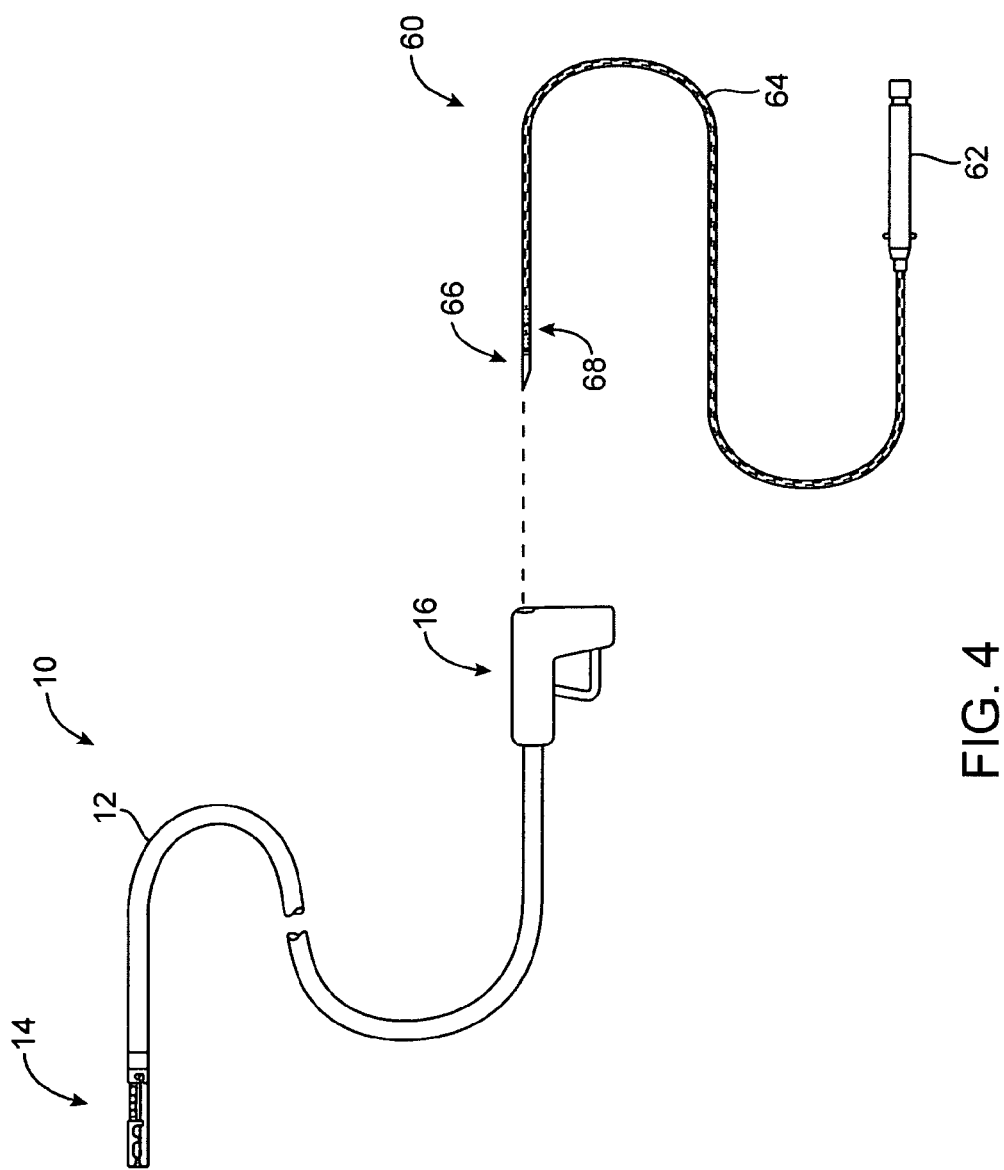

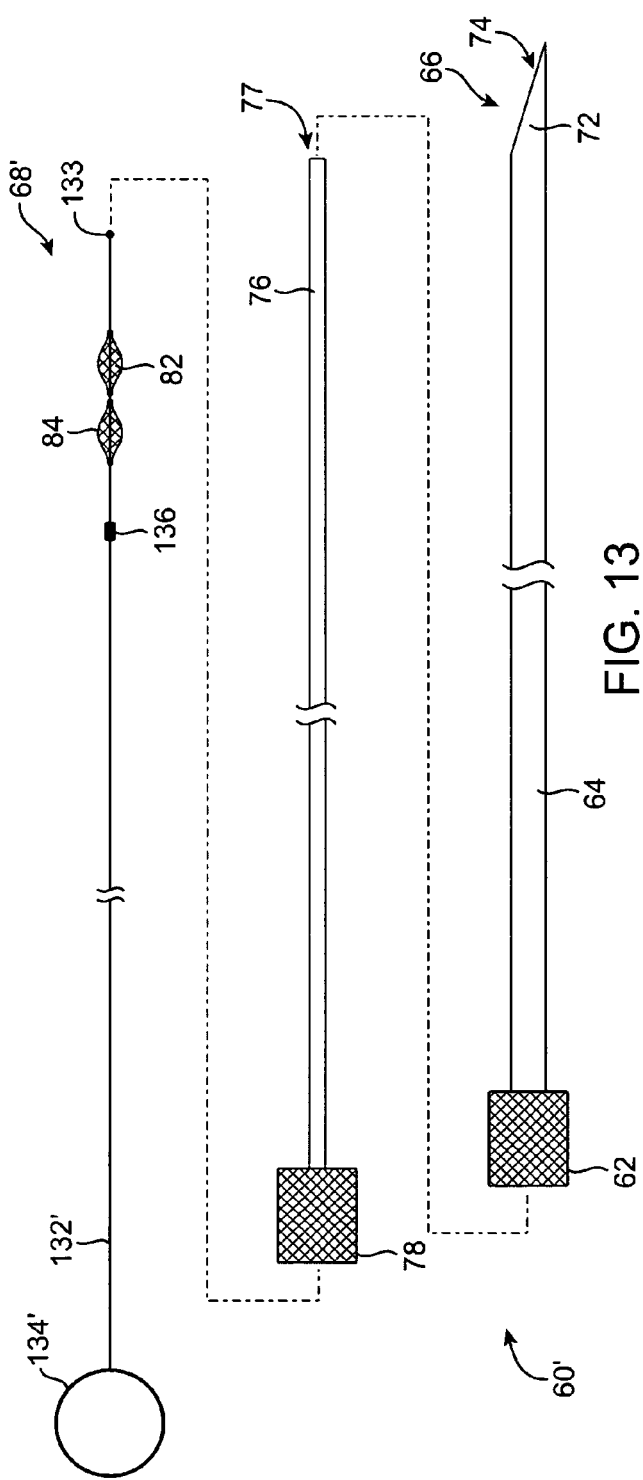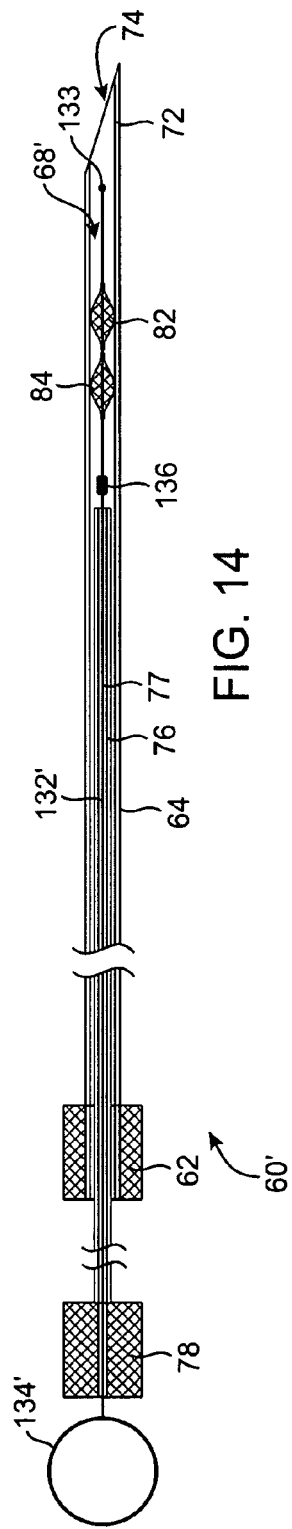
FIG. 13
FIG. 14

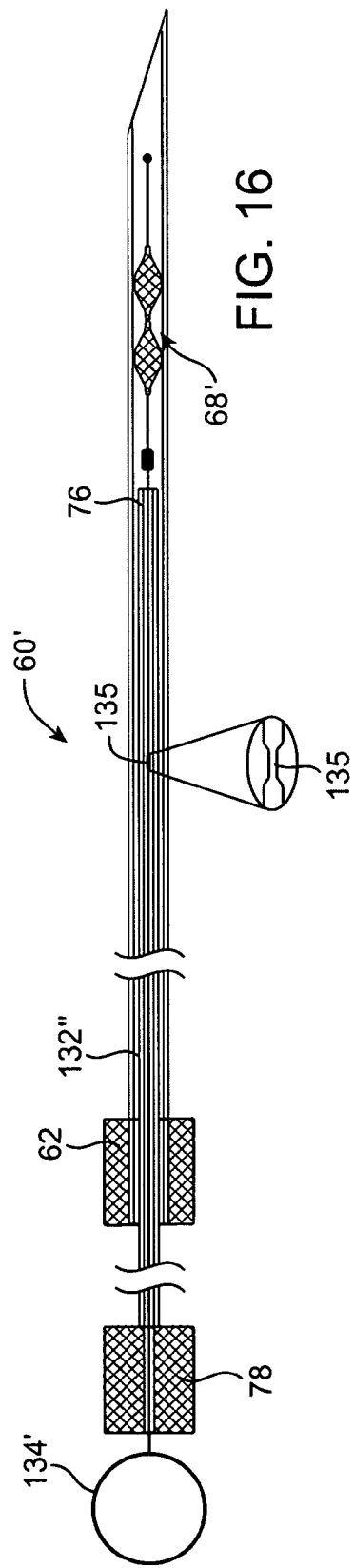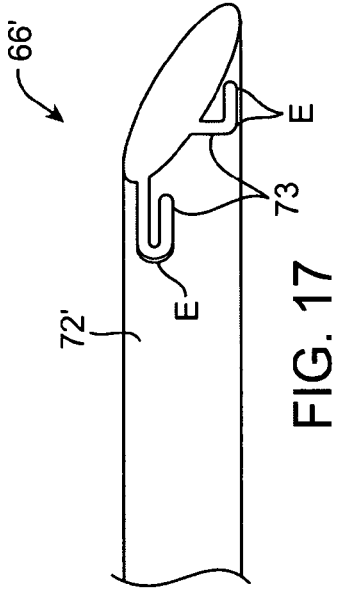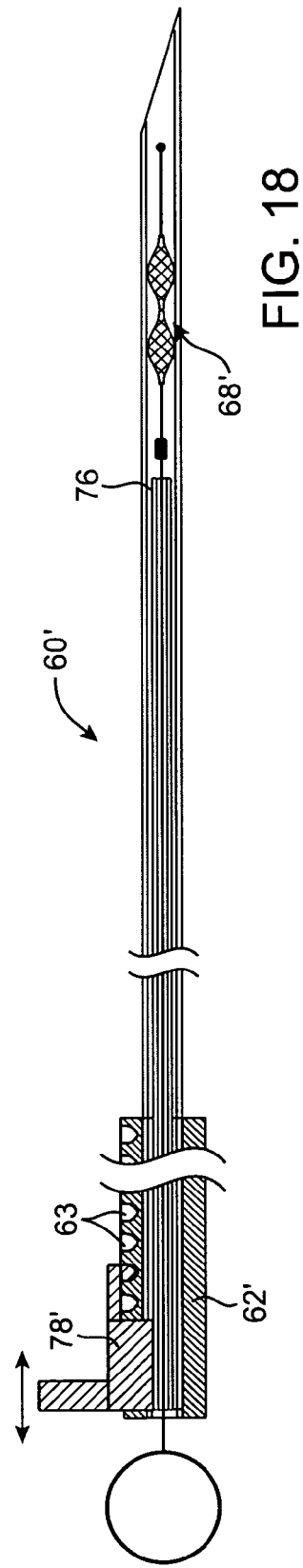

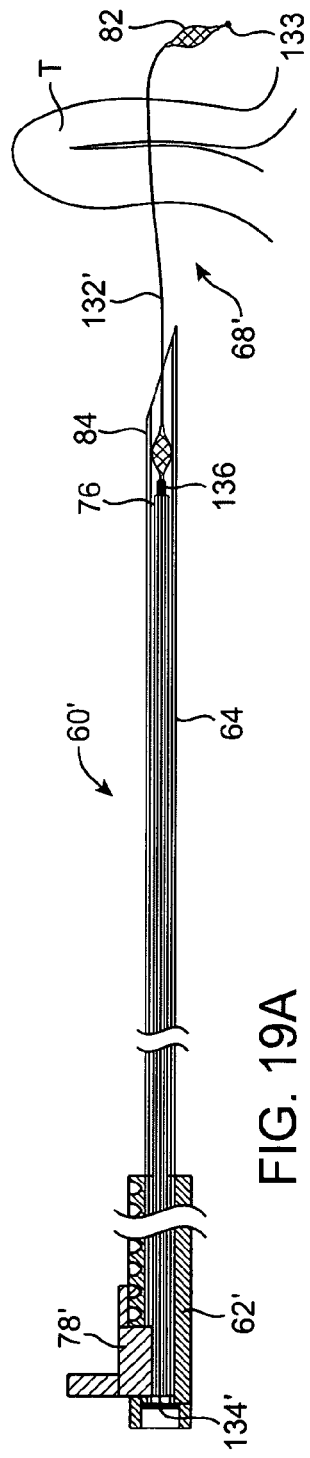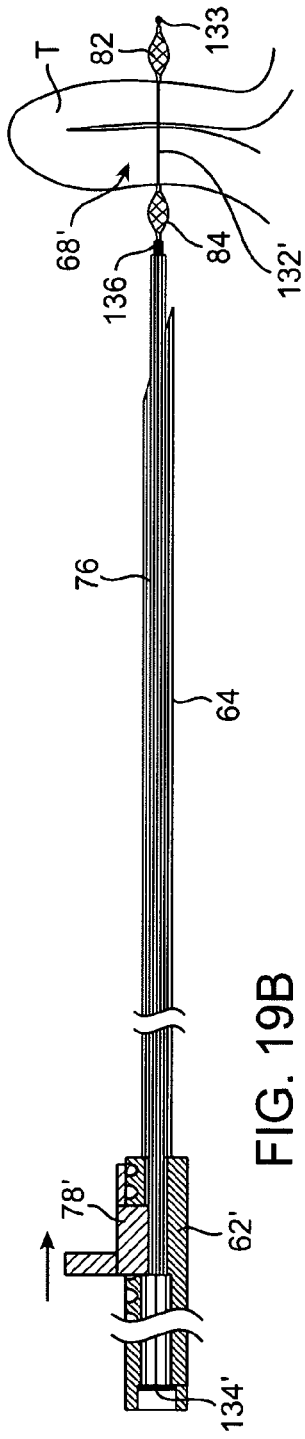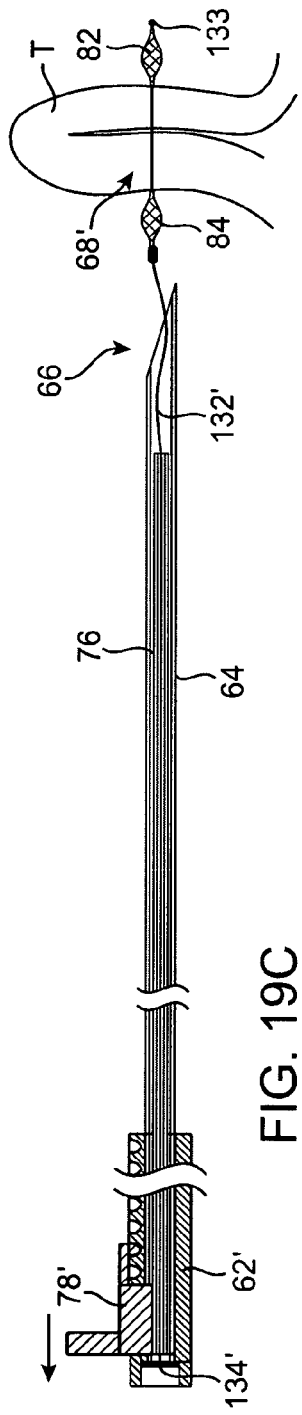

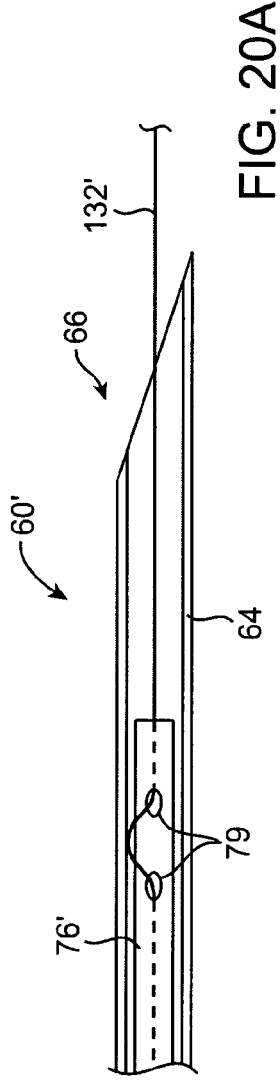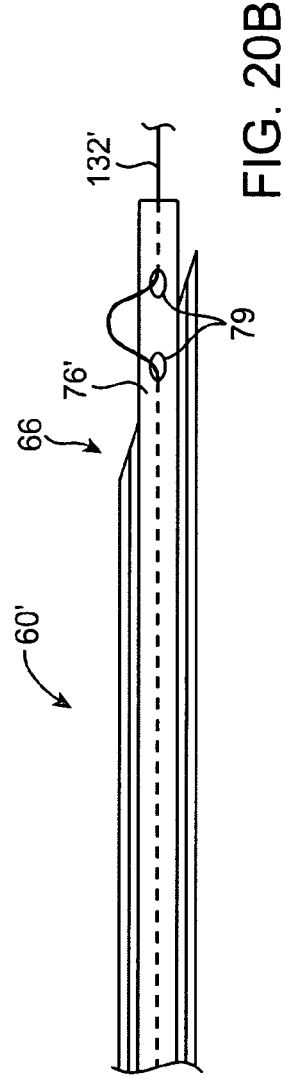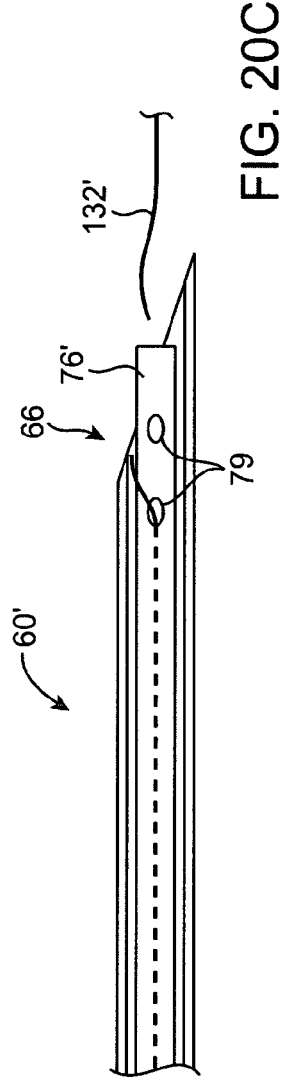

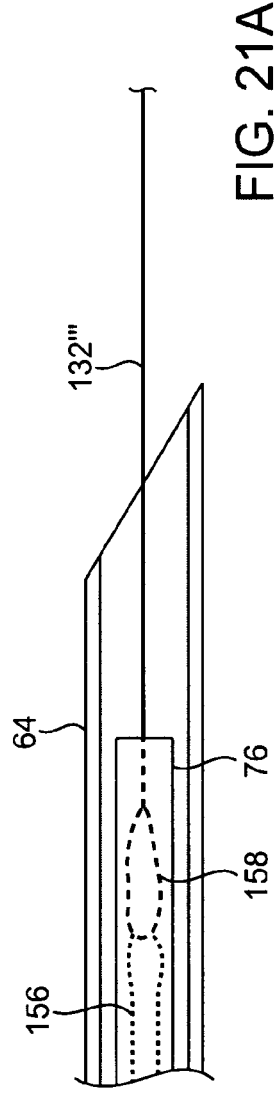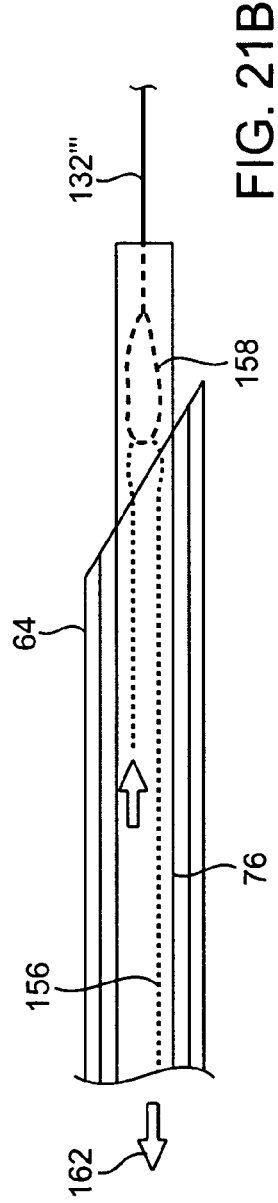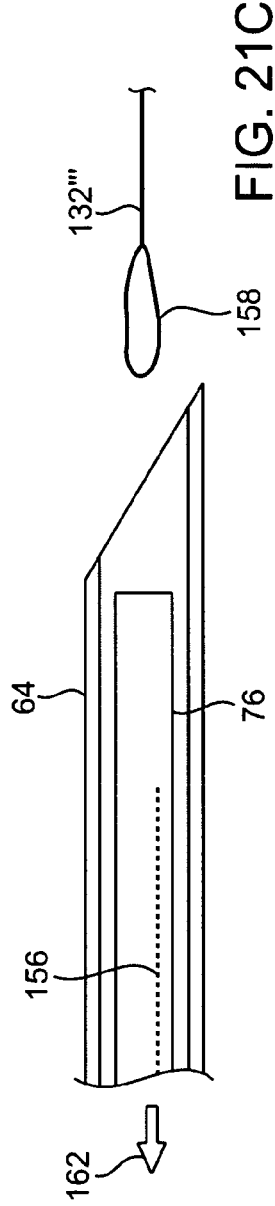

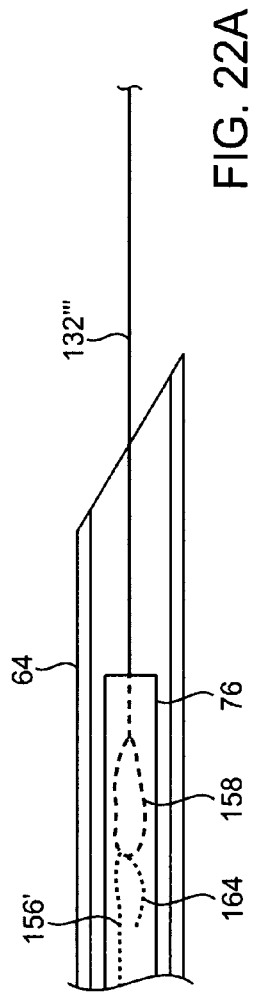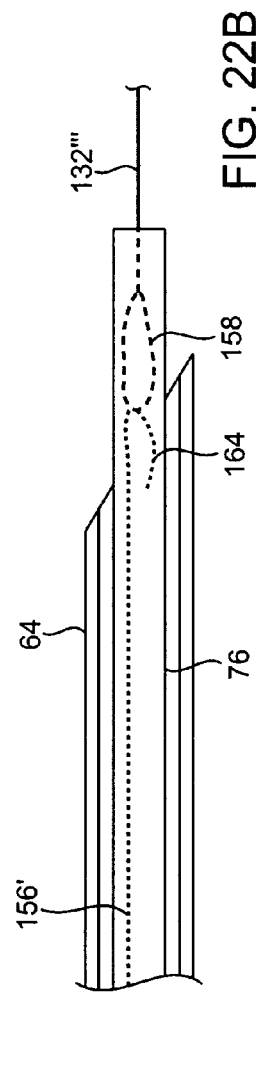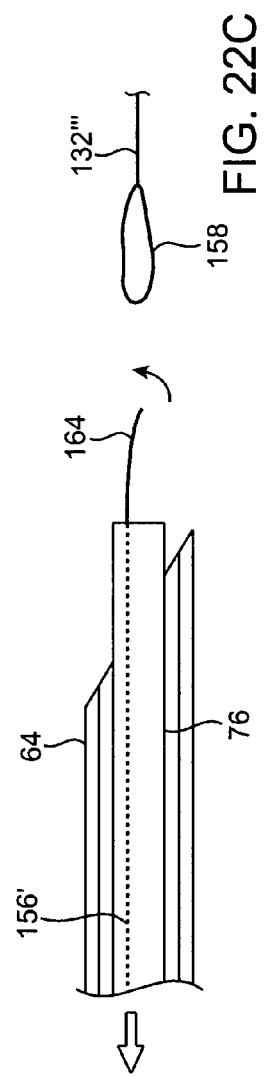

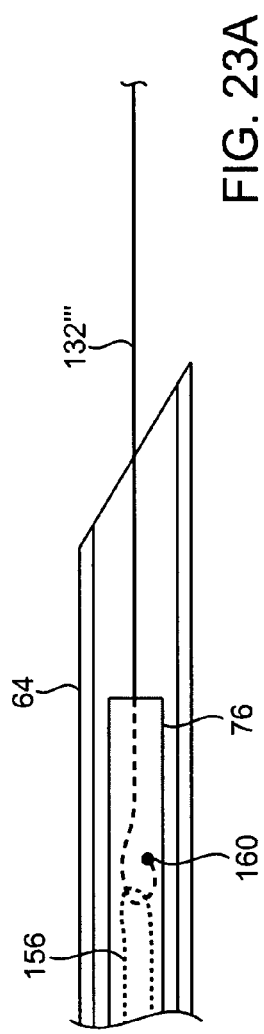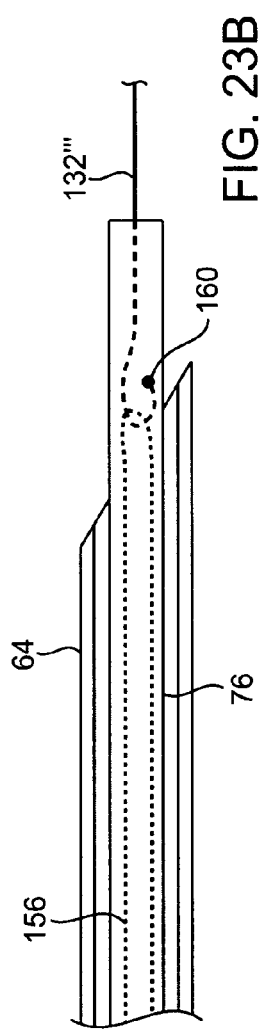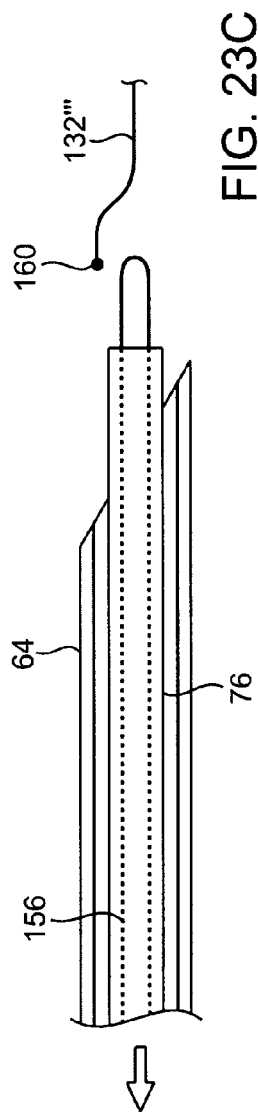

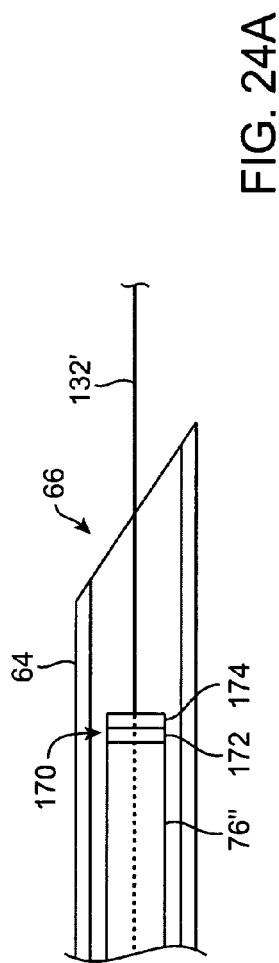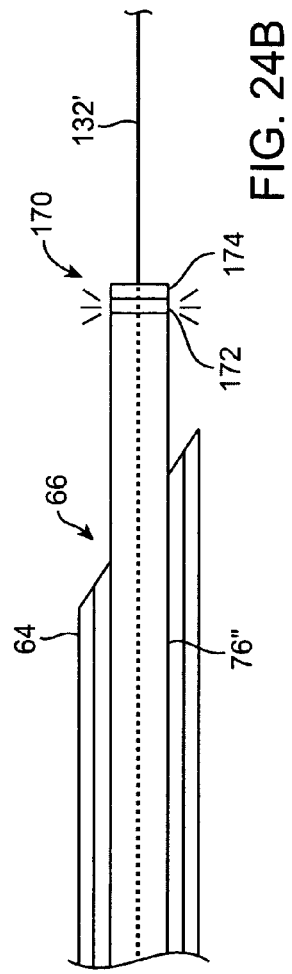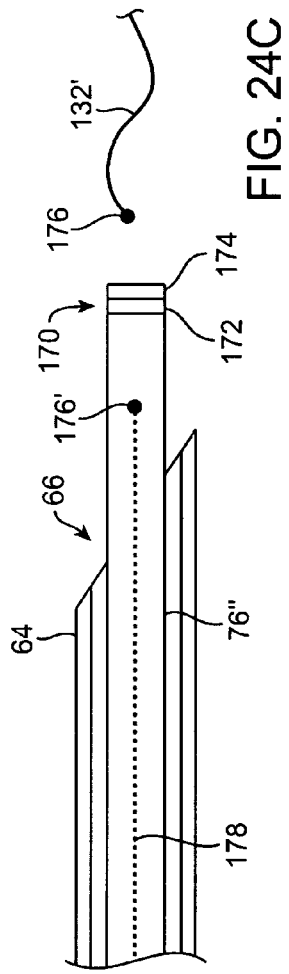

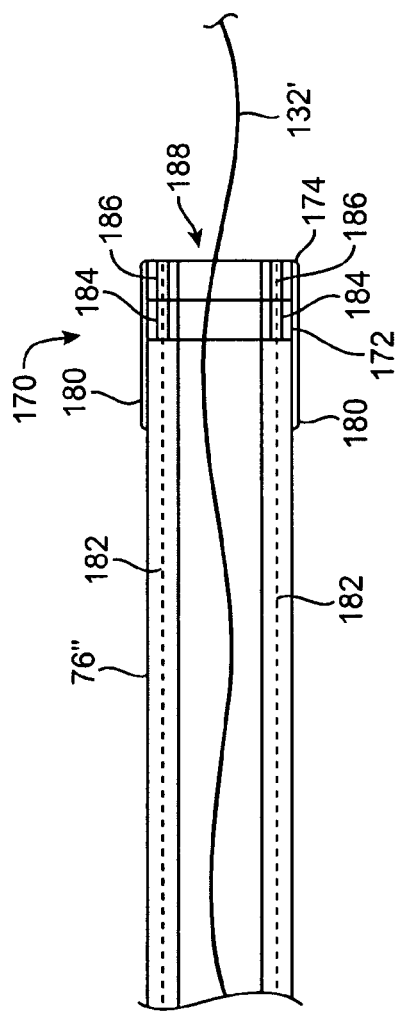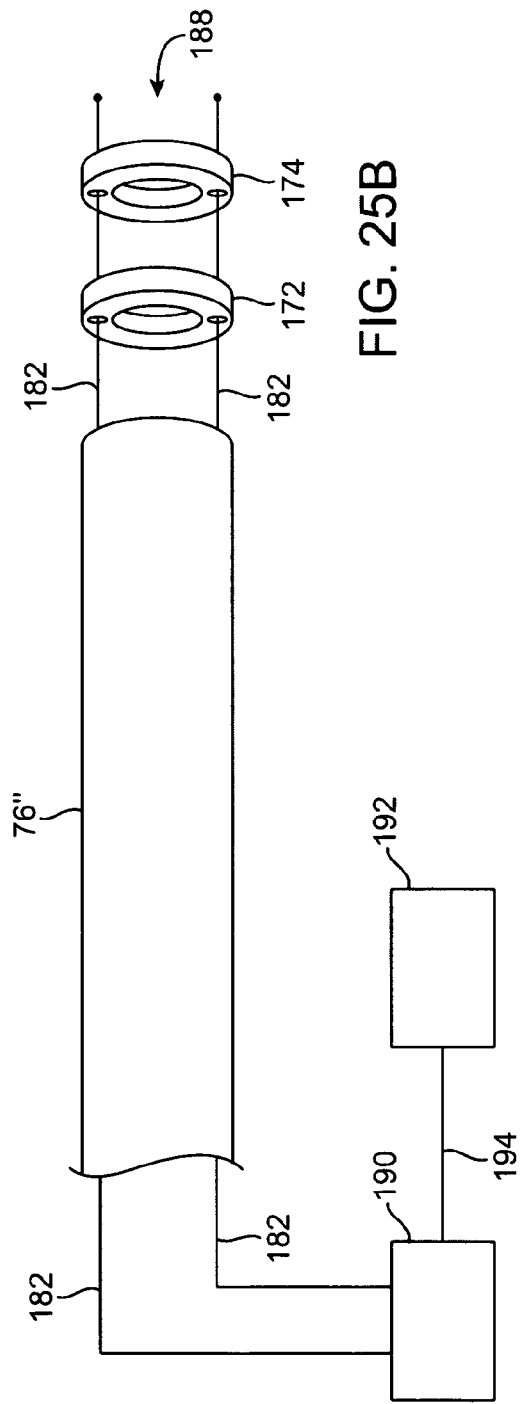

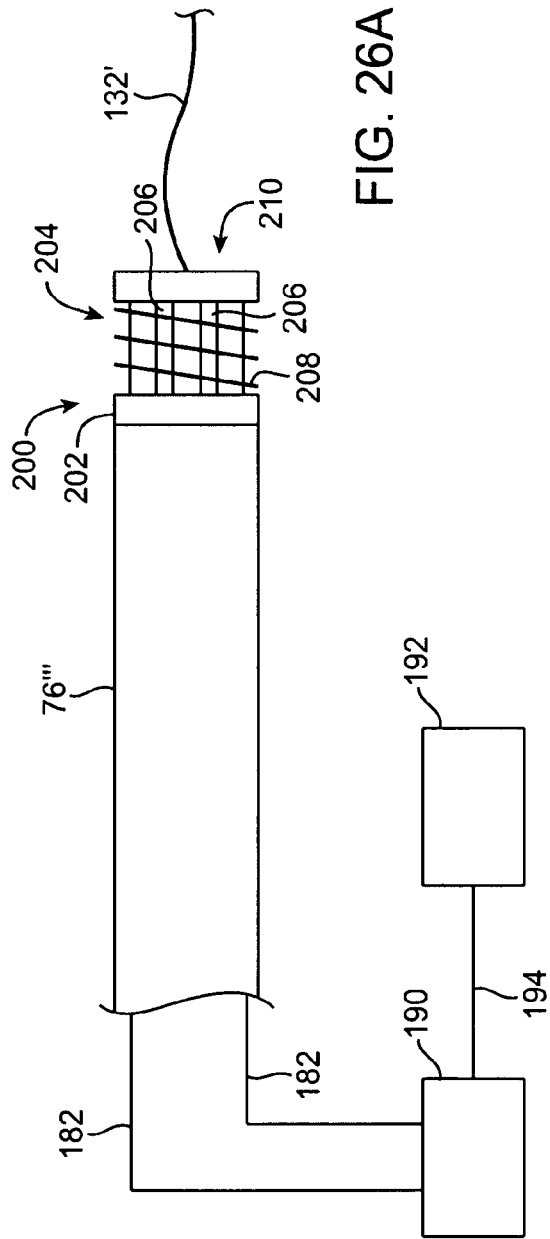
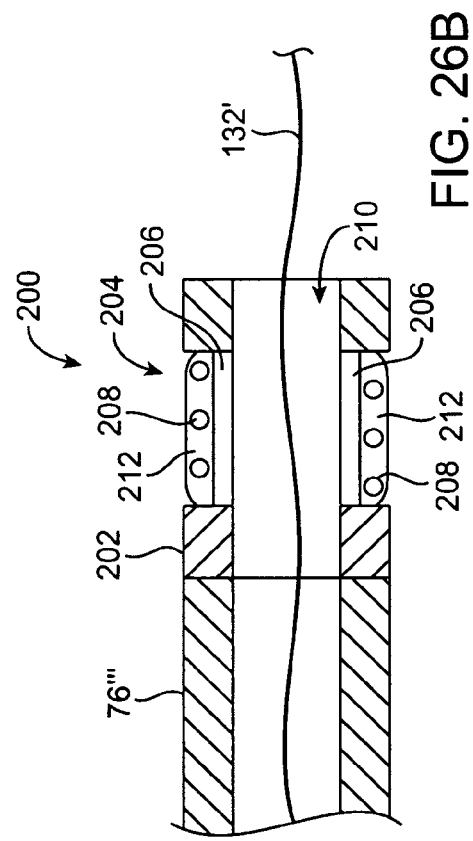

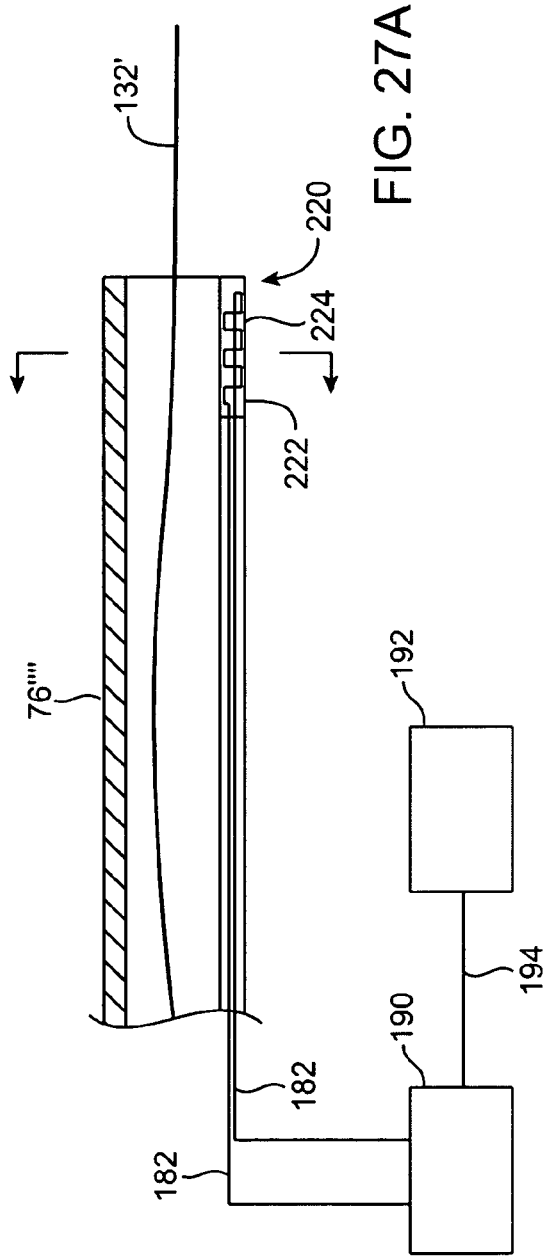
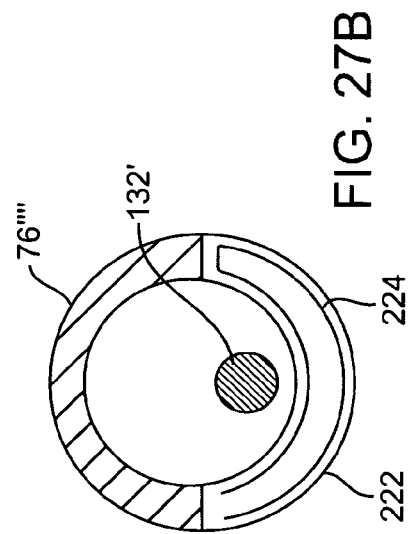

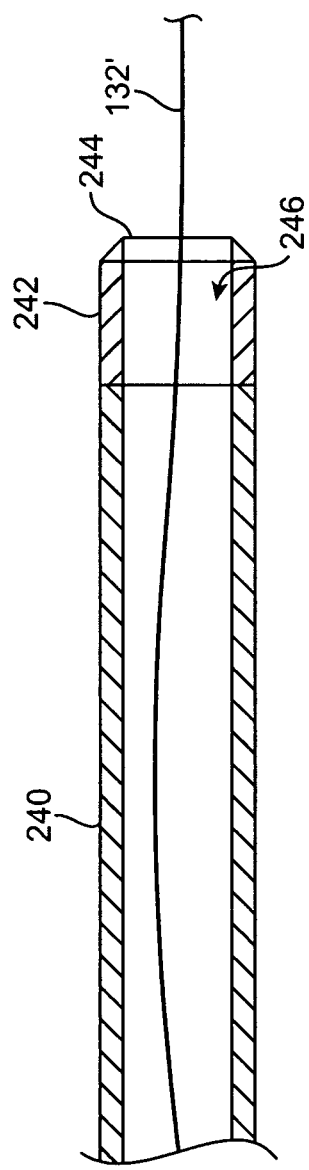
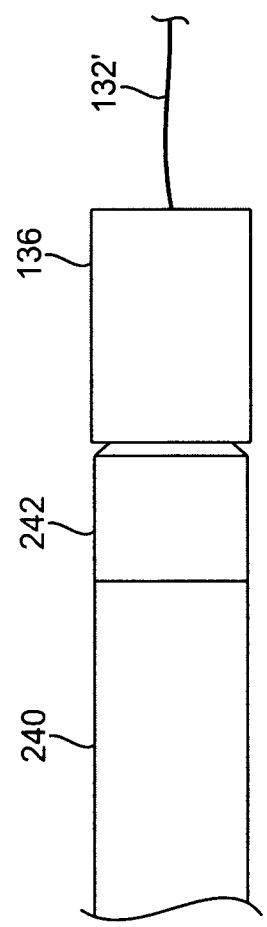
FIG. 29A
FIG. 29B

METHODS AND APPARATUS FOR SECURING AND DEPLOYING TISSUE ANCHORS

CROSS-REFERENCES TO RELATED APPLICATIONS

The present application is a continuation-in-part of U.S. patent application Ser. No. 11/139,920, filed May 26, 2005, which is incorporated herein by reference in its entirety.

BACKGROUND OF THE INVENTION

1. Field of the Invention

The present invention relates to methods and apparatus for securing and deploying tissue anchors. More particularly, the present invention relates to methods and apparatus for endoluminally or laparoscopically securing and deploying anchors within or against tissue, for instance, to form and/or secure tissue folds or to approximate regions of tissue, etc.

A number of surgical techniques have been developed to treat various gastrointestinal disorders. One such example of a pervasive disorder is morbid obesity. Conventional surgical treatment for morbid obesity typically includes, e.g., bypassing an absorptive surface of the small intestine, or reducing the stomach size. However, many conventional surgical procedures may present numerous life-threatening post-operative complications, and may cause atypical diarrhea, electrolytic imbalance, unpredictable weight loss and reflux of nutritious chyme proximal to the site of the anastomosis.

Furthermore, the sutures or staples that are often used in surgical procedures for gastrointestinal disorders typically require extensive training by the clinician to achieve competent use, and may concentrate significant force over a small surface area of the tissue, thereby potentially causing the suture or staple to tear through the tissue. Many of the surgical procedures require regions of tissue within the body to be approximated towards one another and reliably secured. The gastrointestinal lumen, for instance, includes four tissue layers, where the mucosa layer is the inner-most tissue layer followed by connective tissue, the muscularis layer, and where the serosa layer is the outer-most tissue layer.

One problem with conventional gastrointestinal reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesophageally rather than intra-operatively, since care must be taken in piercing the tough stomach wall not to inadvertently puncture adjacent tissue or organs.

One conventional method for securing anchors within a body lumen to the tissue is to utilize sewing devices to suture the stomach wall into folds. This procedure typically involves advancing a sewing instrument through the working channel of an endoscope and into the stomach and against the stomach wall tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen. In the period of time that a patient is anesthetized, procedures such as for the treatment of morbid obesity or for GERD must be performed to completion. Accordingly, the placement and securement of the tissue plication should ideally be relatively quick and performed with a minimal level of confidence.

Another problem with conventional methods involves ensuring that the staple, knotted suture, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally.

Moreover, when grasping or clamping onto or upon the layers of tissue with conventional anchors, sutures, staples, clips, etc., many of these devices are configured to be placed only after the tissue has been plicated and not during the actual plication procedure.

BRIEF SUMMARY OF THE INVENTION

An example of a tool which may be utilized for endoluminally accessing tissue may generally comprise a flexible catheter or tubular body which may be configured to be sufficiently flexible for advancement into a body lumen, e.g., transorally, percutaneously, laparoscopically, etc. The tubular body may be configured to be torqueable such that when a control handle is manipulated and/or rotated by a practitioner from outside the patient's body, the longitudinal and/or torquing force is transmitted along the flexible body such that the distal end of body is advanced, withdrawn, or rotated in a corresponding manner.

A tissue manipulation assembly may be located at the distal end of the tubular body and is generally used to contact and form tissue folds, as mentioned above. The tissue manipulation assembly may be connected to the distal end of the tubular body via a pivotable coupling, and a lower jaw member may extend distally from the pivotable coupling with an upper jaw member, in this example, pivotably coupled to the lower jaw member via a jaw pivot. The location of the jaw pivot may be positioned at various locations along the lower jaw depending upon a number of factors, e.g., the desired size of the "bite" or opening for accepting tissue between the jaw members, the amount of closing force between the jaw members, etc. One or both jaw members may also have a number of protrusions, projections, grasping teeth, textured surfaces, etc., on the surface or surfaces of the jaw members to facilitate the adherence of tissue therebetween.

A launch tube may extend from the handle, through tubular body, and distally from the end of tubular body where a distal end of the launch tube is pivotally connected to the upper jaw member at a pivot. A distal portion of the launch tube may be pivoted into position within a channel or groove defined in upper jaw member to facilitate a low-profile configuration of the tissue manipulation assembly. When articulated, either via the launch tube or other mechanism, the jaw members may be urged into an open configuration to receive tissue in the jaw opening between the jaw members.

In operation, a shape-lockable endoscopic assembly may be advanced into a patient's stomach per-orally and through the esophagus. Such an endoscopic assembly may generally comprise an endoscopic device, which may have a distal portion that may be articulated and steered to position its distal end anywhere within the stomach. Once desirably configured, the assembly may then be locked or rigidized to maintain its shape or configuration to allow for procedures to be performed on the tissue utilizing any number of tools delivered therethrough.

The tissue manipulation assembly may be delivered into the patient while in a low-profile configuration, e.g., transorally, through the shape-lockable endoscopic assembly, through an endoscope, an endoscopic device, or directly. Once desirably positioned, the launch tube may be urged proximally via its proximal end at handle. Because the jaw assembly pivot and the relative positioning of the upper jaw pivot along lower jaw member and launch tube pivot along upper jaw member, the proximal movement of the launch tube may effectively articulate upper jaw into an expanded jaw configuration. Proximally urging the launch tube may also urge the lower jaw member to pivot about the assembly pivot and form an angle relative to a longitudinal axis of the tubular body. The opening of the upper jaw relative to the lower jaw creates a jaw opening for grasping or receiving tissue. Moreover, the tissue manipulation assembly may also include a stop located adjacent to the jaw assembly pivot or within the pivot itself.

A second tool for initially engaging the tissue region of interest may also be deployed and utilized to engage the tissue and to position the engaged tissue between the jaws of the jaw assembly. Any number of tools may be used in combination with the tissue manipulation assembly. Once the tissue has been engaged between the jaw members, a needle assembly may be urged through the launch tube to pierce through the grasped tissue. Once the needle assembly has been passed through the engaged tissue, one or more tissue anchors may be deployed for securing the tissue.

Once the one or more tissue anchors having been deployed, the tissue may be secured via an anchor deployment assembly, which may generally comprise an elongate member adapted for advancement within a body lumen of the patient and being further adapted to deploy at least one tissue anchor having a length of suture depending therefrom, wherein the elongate member comprises a suture cutting element disposed thereon which is adapted to sever a portion of the suture via thermal energy.

BRIEF DESCRIPTION OF THE DRAWINGS

FIG. 4 shows an assembly view of how a needle deployment assembly may be introduced through a handle and tubular body of the tissue manipulation assembly.

FIG. 13 illustrates an exploded view of a variation of an anchor assembly and needle deployment assembly.

FIG. 14 illustrates an assembly view, partially in section, of the anchor assembly and needle deployment assembly variation of FIG. 13.

FIG. 16 illustrates a variation of the suture element for use with the anchor assembly and needle deployment assembly of FIGS. 13 to 15.

FIG. 17 illustrates a variation of the needle for use with the anchor assembly and needle deployment assembly variation of FIGS. 13 to 15.

FIG. 18 illustrates a variation of the control mechanisms for use with the needle deployment assemblies of FIGS. 13 to 17.

FIGS. 19A to 19C illustrate an exemplary method of using another variation of the anchor assembly and needle deployment assembly.

FIGS. 20A to 20C are schematic views illustrating another variation of the needle deployment assembly.

FIGS. 21A to 21C illustrate another variation of the needle deployment assembly utilizing a release suture or wire which may be routed through a looped terminal end of a suture element.

FIGS. 22A to 22C illustrate yet another variation of the needle deployment assembly utilizing a reconfigurable hook element which may configure itself from a hooked configuration to an open or straightened configuration.

FIGS. 23A to 23C illustrate yet another variation of the needle deployment assembly utilizing a release suture or wire with an obstructive element to be released from the release suture or wire.

FIGS. 24A to 24C illustrate yet another variation of the needle deployment assembly utilizing a suture cutting thermal element for releasing the suture and anchor assembly.

FIGS. 25A and 25B show partial cross-sectional side and assembly views, respectively, of the suture cutting thermal element assembly of FIGS. 24A to 24C.

FIGS. 26A and 26B show side and partial cross-sectional views, respectively, of another suture cutting thermal element.

FIGS. 27A and 27B show partial cross-sectional side and end views of yet another suture cutting thermal element.

FIG. 29A shows another pusher variation having a circumferential cutting edge disposed at the distal end of the pusher.

FIG. 29B shows the instrument of FIG. 29A abutted against a locking mechanism for cinching of the tissue anchors against a tissue surface.

DETAILED DESCRIPTION OF THE INVENTION

In manipulating tissue or creating tissue folds, a having a distal end effector may be advanced endoluminally, e.g., transorally, transgastrically, etc., into the patient's body, e.g., the stomach. The tissue may be engaged or grasped and the engaged tissue may be manipulated by a surgeon or practitioner from outside the patient's body. Examples of creating and forming tissue plications may be seen in further detail in U.S. patent application Ser. No. 10/955,245 filed Sep. 29, 2004, which has been incorporated herein by reference above, as well as U.S. patent application Ser. No. 10/735,030 filed Dec. 12, 2003, which is incorporated herein by reference in its entirety.

In engaging, manipulating, and/or securing the tissue, various methods and devices may be implemented. For instance, tissue securement devices may be delivered and positioned via an endoscopic apparatus for contacting a tissue wall of the gastrointestinal lumen, creating one or more tissue folds, and deploying one or more tissue anchors through the tissue fold(s). The tissue anchor(s) may be disposed through the muscularis and/or serosa layers of the gastrointestinal lumen.

Figure 1A:
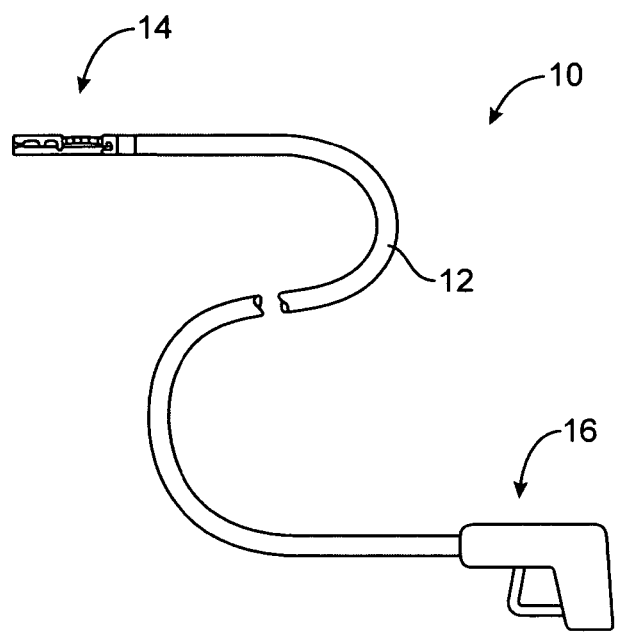
FIG. 1A shows a side view of one variation of a tissue manipulation assembly having a flexible body and a handle.

An illustrative side view of one example of a tool which may be utilized for endoluminally accessing tissue is shown in FIG. 1A, which shows assembly 10. The assembly 10 generally comprises a flexible catheter or tubular body 12 which may be configured to be sufficiently flexible for advancement into a body lumen, e.g., transorally, percutaneously, laparoscopically, etc. Tubular body 12 may be configured to be torqueable through various methods, e.g., utilizing a braided tubular construction, such that when handle 16 is manipulated and/or rotated by a practitioner from outside the patient's body, the longitudinal and/or torquing force is transmitted along body 12 such that the distal end of body 12 is advanced, withdrawn, or rotated in a corresponding manner.

Figure 1B:
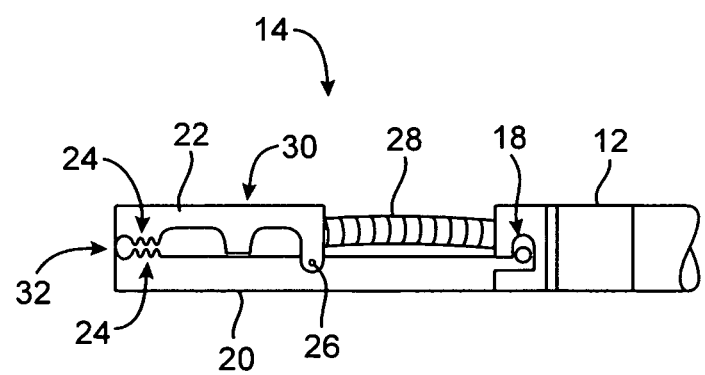
FIG. 1B illustrates a detail side view of a tissue manipulation assembly in a low-profile configuration connected to the distal end of the tubular body via a pivotable coupling.

Tissue manipulation assembly 14 is located at the distal end of tubular body 12 and is generally used to contact and form tissue folds, as mentioned above. FIG. 1B shows an illustrative detail side view in which tissue manipulation assembly 14 may be seen connected to the distal end of tubular body 12 via a pivotable coupling 18. Lower jaw member 20 extends distally from the pivotable coupling 18 and upper jaw member 22, in this example, may be pivotably coupled to lower jaw member 20 via jaw pivot 26. The location of jaw pivot 26 may be positioned at various locations along lower jaw 20 depending upon a number of factors, e.g., the desired size of the "bite" or opening for accepting tissue between the jaw members, the amount of closing force between the jaw members, etc. One or both jaw members 20, 22 may also have a number of protrusions, projections, grasping teeth, textured surfaces, etc., 24 on the surface or surfaces of the jaw members 20, 22 facing one another to facilitate the adherence of tissue between the jaw members 20, 22.

Launch tube 28 may extend from handle 16, through tubular body 12, and distally from the end of tubular body 12 where a distal end of launch tube 28 is pivotally connected to upper jaw member 22 at launch tube pivot 30. A distal portion of launch tube 28 may be pivoted into position within a channel or groove defined in upper jaw member 22, to facilitate a low-profile configuration of tissue manipulation assembly 14. When articulated, either via launch tube 28 or other mechanism, as described further below, jaw members 20, 22 may be urged into an open configuration to receive tissue in jaw opening 32 between the jaw members 20, 22.

Launch tube 28 may be advanced from its proximal end at handle 16 such that the portion of launch tube 28, which extends distally from body 12, is forced to rotate at hinge or pivot 30 and reconfigure itself such that the exposed portion forms a curved or arcuate shape that positions the launch tube opening perpendicularly relative to upper jaw member 22. Launch tube 28, or at least the exposed portion of launch tube 28, may be fabricated from a highly flexible material or it may be fabricated, e.g., from Nitinol tubing material which is adapted to flex, e.g., via circumferential slots, to permit bending.

Figure 2A:
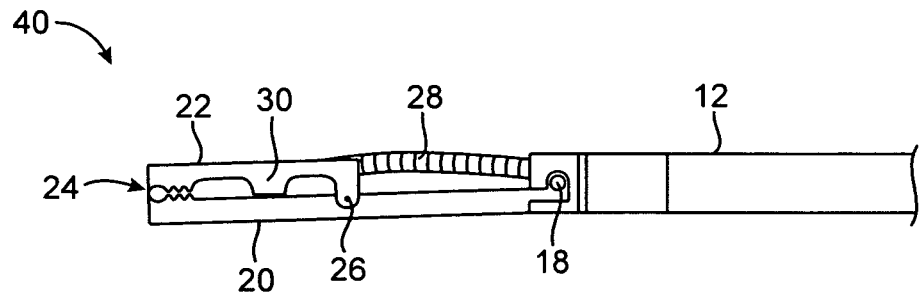
FIGS. 2A to 2C illustrate a method for articulating the tissue manipulation assembly from a low-profile configuration to an opened configuration and to a closed jaw configuration for clamping upon tissue, respectively.
Figure 2B:
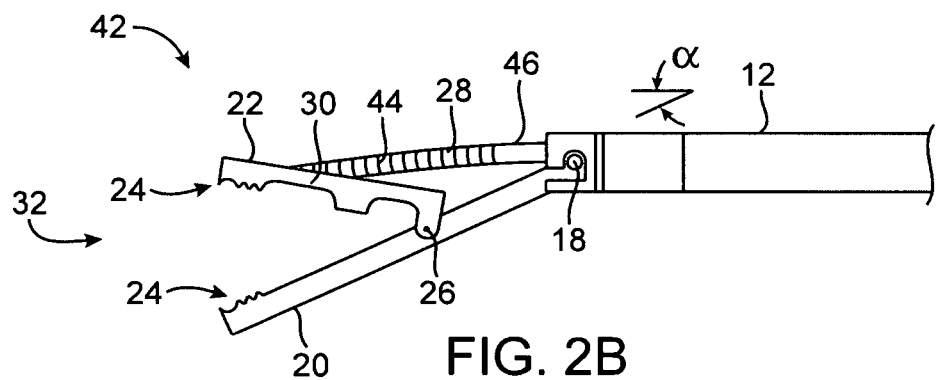
Figure 2C:
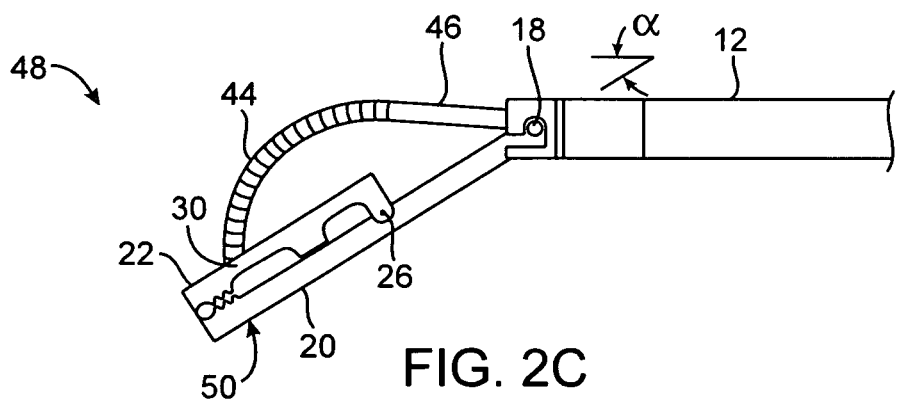

FIGS. 2A to 2C illustrate one method for articulating a tissue manipulation assembly into an opened and closed configuration. As shown in FIG. 2A, the assembly may be delivered into a patient while in a low-profile configuration 40, e.g., transorally, through an endoscope, an endoscopic device, or directly. Once desirably positioned, launch tube 28 may be urged proximally via its proximal end at handle 16. Because of jaw assembly pivot 18 and the relative positioning of upper jaw pivot 26 along lower jaw member 20 and launch tube pivot 30 along upper jaw member 22, the proximal movement of launch tube 28 may effectively articulate upper jaw 22 into an expanded jaw configuration 42, as shown in FIG. 2B. Proximally urging launch tube 28 may also urge lower jaw member 20 to pivot about assembly pivot 18 and form an angle, a, relative to a longitudinal axis of tubular body 12. The opening of upper jaw 22 relative to lower jaw 20 creates jaw opening 32 for grasping or receiving tissue. Moreover, the tissue manipulation assembly may also include a stop located adjacent to jaw assembly pivot 18 or within the pivot 18 itself.

Once launch tube 28 has been urged proximally, it may be locked into place thus locking the jaw configuration as well. Moreover, having the launch tube 28 articulate the jaw members 20, 22 in this variation eliminates the need for a separate jaw articulation and/or locking mechanism. Once the tissue has been pulled or manipulated between jaw members 20, 22, launch tube 28 may be pushed distally to actuate the jaw members 20, 22 into a closed, grasping configuration 48, as shown in FIG. 2C, for engagement with the tissue. As launch tube 28 is urged distally through body 12, lower jaw member 20 may be maintained at the angle, α, relative to the tissue to further facilitate manipulation of the grasped tissue.

Launch tube 28 may further define a flexible portion 44 distally of a rigid portion 46. Although launch tube 28 may be fabricated from different materials having differing flexibilities, it may also be fabricated from a single material, as mentioned above, where the flexible portion 44 may configured, e.g., by slotting, to allow for bending of the launch tube 28 in a plane to form a single curved or arcuate section while the rigid section 46 may extend at least partially into tubular body 12 to provide column strength to launch tube 28 while it is urged distally upon upper jaw member 22 and upon any tissue engaged thereby, as seen in the FIG. 2C.

Once the tissue has been engaged between jaw members 20, 22, a needle assembly may be urged through handle 16 and out through launch tube 28. The needle assembly may pass through lower jaw member 20 via needle assembly opening 50 defined in lower jaw member 20 to pierce through the grasped tissue. Once the needle assembly has been passed through the engaged tissue, one or more tissue anchors may be deployed for securing the tissue, as described in further detail in U.S. patent application Ser. No. 10/955,245, which has been incorporated by reference above.

Figure 3A:
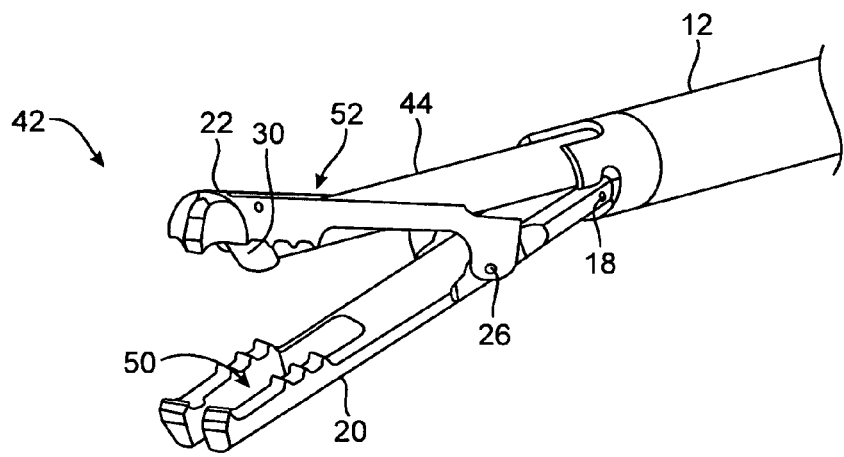
FIGS. 3A and 3B show detail perspective views of the tissue manipulation assembly in an open and clamped configuration, respectively.
Figure 3B:
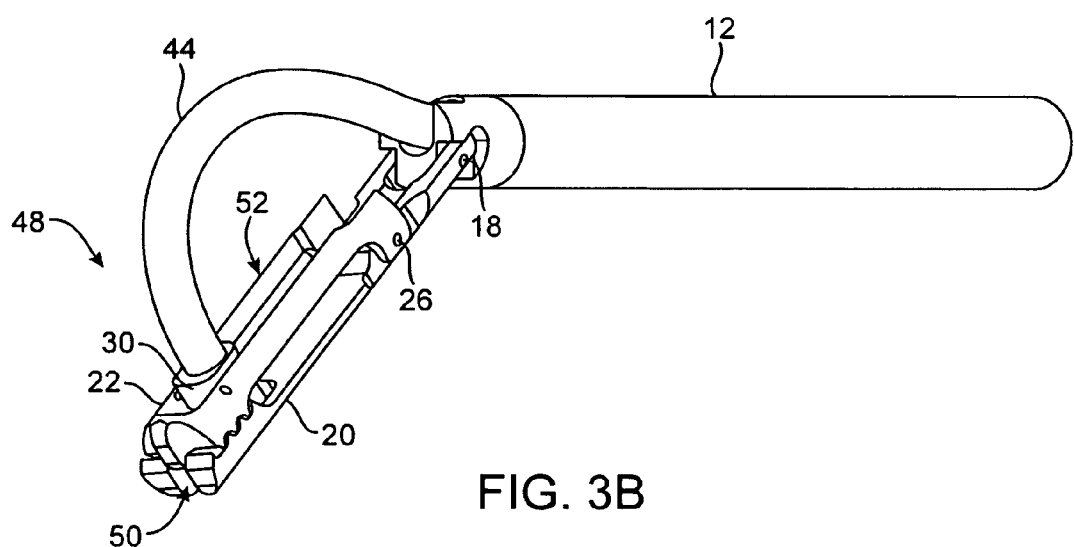

FIGS. 3A and 3B show detail perspective views of the tissue manipulation assembly. As shown in FIG. 3A, lower jaw member 20 and upper jaw member 22 may be seen its open configuration 42 when the launch tube has been urged proximally. Launch tube channel 52 may also be seen defined within upper jaw member 22 for providing a space for positioning the launch tube when in the low-profile configuration. Also shown is needle assembly opening 50 defined within lower jaw member 20 for passage of the needle assembly therethrough. FIG. 3B shows the assembly in its closed jaw configuration where the launch tube has been urged distally in which it rotates about launch tube pivot 30 such that the opening the launch tube become perpendicular relative to the jaw members 20, 22.

Although one particular variation of the jaw members 20, 22 is shown, this is not intended to be limiting in jaw member configuration or operation. Other variations may include various placement of the jaws relative to one another, alternative configurations for articulating the jaw members, alternative configurations for the launch tube placement, etc. Other variations are intended to be within the scope of this disclosure.

As mentioned above, a needle deployment assembly 60 may be deployed through the assembly 10 by introducing needle deployment assembly 60 into the handle 16 and through tubular body 12, as shown in the assembly view of FIG. 4, such that the needle assembly 66 is advanced from the launch tube and into or through approximated tissue. Once the needle assembly 66 has been advanced through the tissue, the anchor assembly 68 may be deployed or ejected. Anchor assembly 68 is normally positioned within the distal portion of tubular sheath 64, which extends from needle assembly control or housing 62. Once the anchor assembly 68 has been fully deployed from sheath 64, the spent needle deployment assembly 60 may be removed from assembly 10 and another needle deployment assembly may be introduced without having to remove assembly 10 from the patient. The length of sheath 64 is such that it may be passed entirely through the length of tubular body 12 to enable the deployment of needle assembly 66 into and/or through the tissue.

Figure 5A:
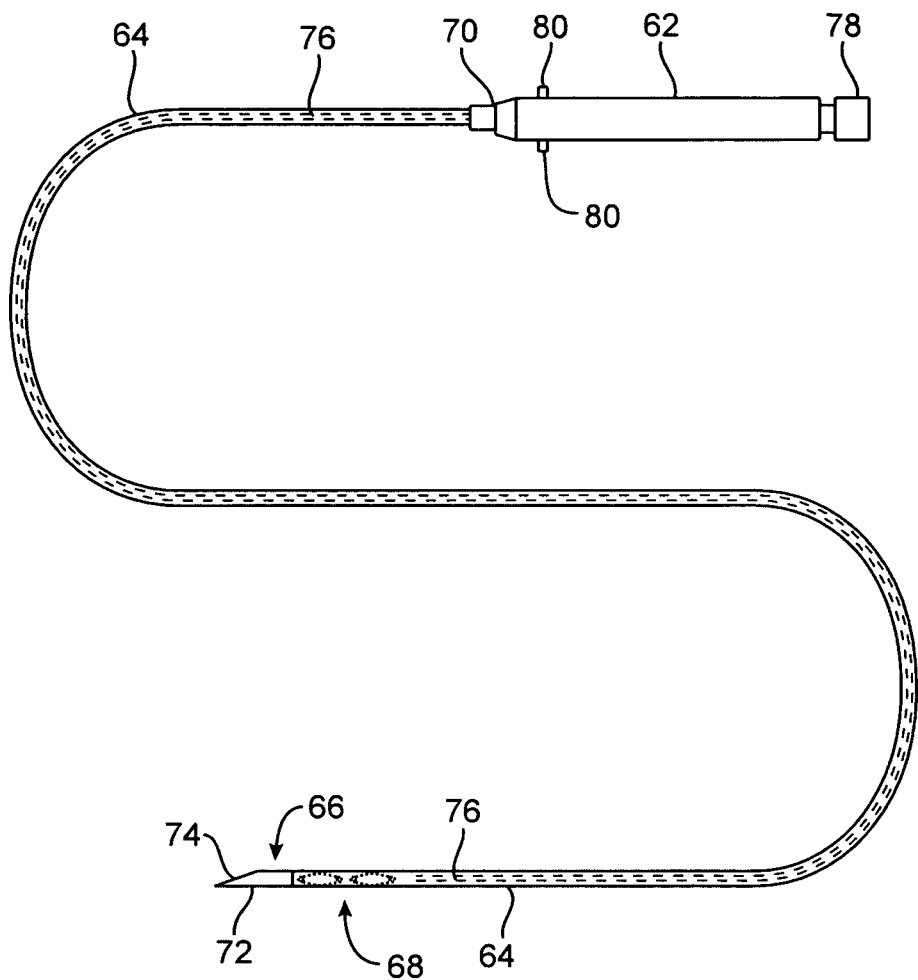
FIG. 5A shows a detailed assembly view of the needle deployment assembly from FIG. 4.

FIG. 5A shows a detailed assembly view of the needle deployment assembly 60 from FIG. 4. In this variation, elongate and flexible sheath or catheter 64 may extend removably from needle assembly control or housing 62. Sheath or catheter 64 and housing 62 may be interconnected via interlock 70 which may be adapted to allow for the securement as well as the rapid release of sheath 64 from housing 62 through any number of fastening methods, e.g., threaded connection, press-fit, releasable pin, etc. Needle body 72, which may be configured into any one of the variations described above, may extend from the distal end of sheath 64 while maintaining communication between the lumen of sheath 64 and needle opening 74.

Figure 5B:
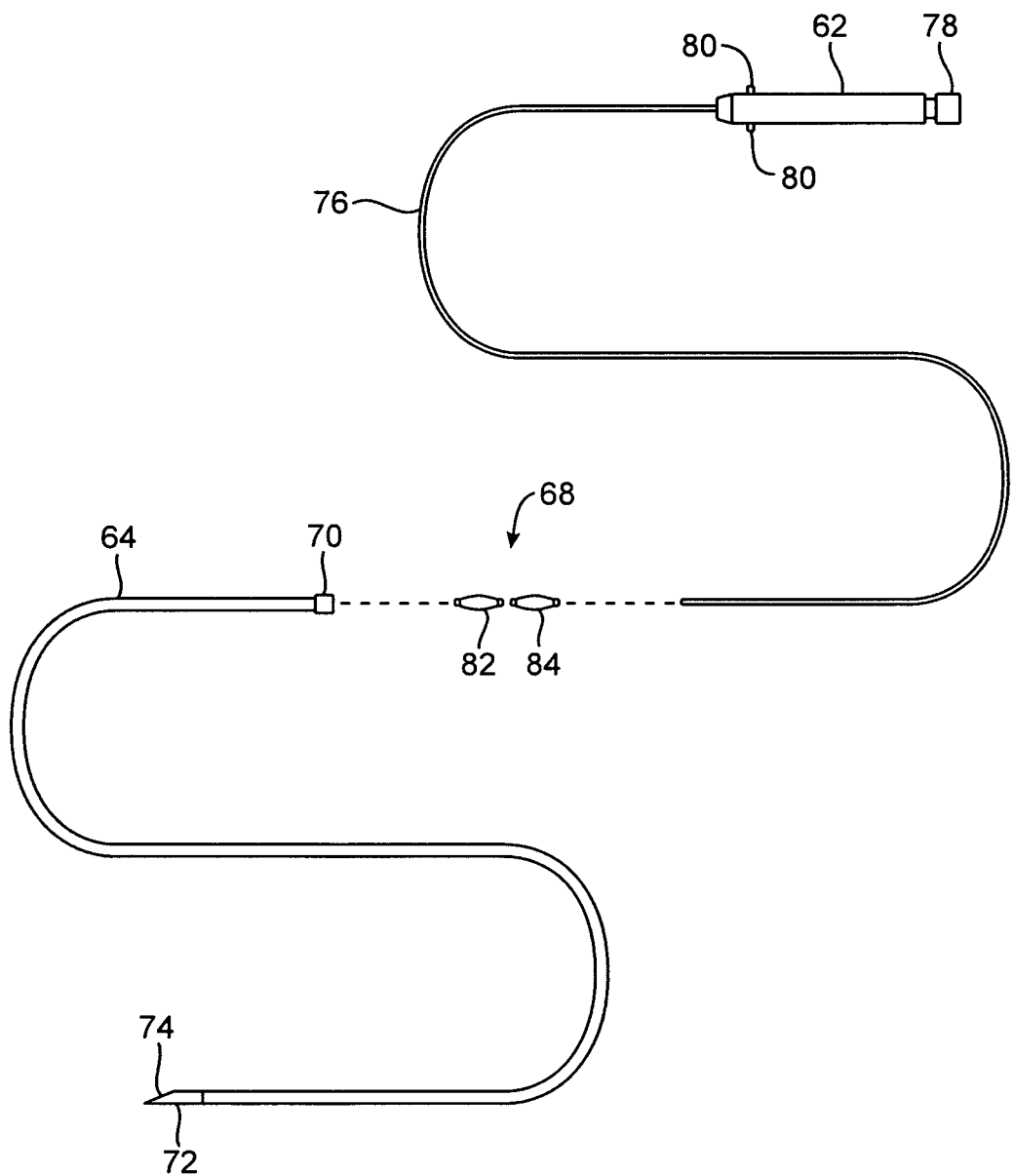
FIG. 5B shows an exploded assembly view of the needle deployment assembly from FIG. 5A.

Elongate pusher 76 may comprise a flexible wire or hypotube which is translationally disposed within sheath 64 and movably connected within housing 62. A proximally-located actuation member 78 may be rotatably or otherwise connected to housing 62 to selectively actuate the translational movement of elongate pusher 76 relative to sheath 64 for deploying the anchors from needle opening 74. Anchor assembly 68 may be seen positioned distally of elongate pusher 76 within sheath 64 for deployment from sheath 64. Needle assembly guides 80 may also be seen protruding from housing 62 for guidance through the locking mechanism described above. FIG. 5B shows an exploded assembly view of the needle deployment assembly 60 from FIG. 5A. As seen, sheath 64 may be disconnected from housing 62 via interlock 70 to reveal the elongate pusher 76 connected to housing 62 and the distal and proximal anchors 82, 84, respectively, of anchor assembly 68.

With respect to the anchor assemblies, the types of anchors shown and described are intended to be illustrative and are not limited to the variations shown. For instance, the tissue anchor variations may also include "T"-type anchors while other variations may include reconfigurable "basket"-type anchors, which may generally comprise a number of configurable struts or legs extending between at least two collars or support members or reconfigurable mesh structures extending between the two collars. Other variations of these or other types of anchors are also contemplated for use in an anchor assembly. Moreover, a single type of anchor may be used exclusively in an anchor assembly; alternatively, a combination of different anchor types may be used in an anchor assembly. Furthermore, the different types of cinching or locking mechanisms are not intended to be limited to any of the particular variations shown and described but may be utilized in any of the combinations or varying types of anchors as practicable.

Other variations for the needle assemblies and for the anchors are described in further detail in U.S. patent application Ser. No. 10/955,245, which has been incorporated by reference above.

In operation when manipulating and securing tissue within a patient's body, a separate elongate shaft having a tool on or near the distal end of the shaft may be utilized in conjunction with the tissue manipulation assembly 14. Such tools are generally utilized in endoluminal procedures where the tools are delivered through an endoscope. Generally, several different tools may be utilized for performing a procedure endoluminally.

Figure 6:
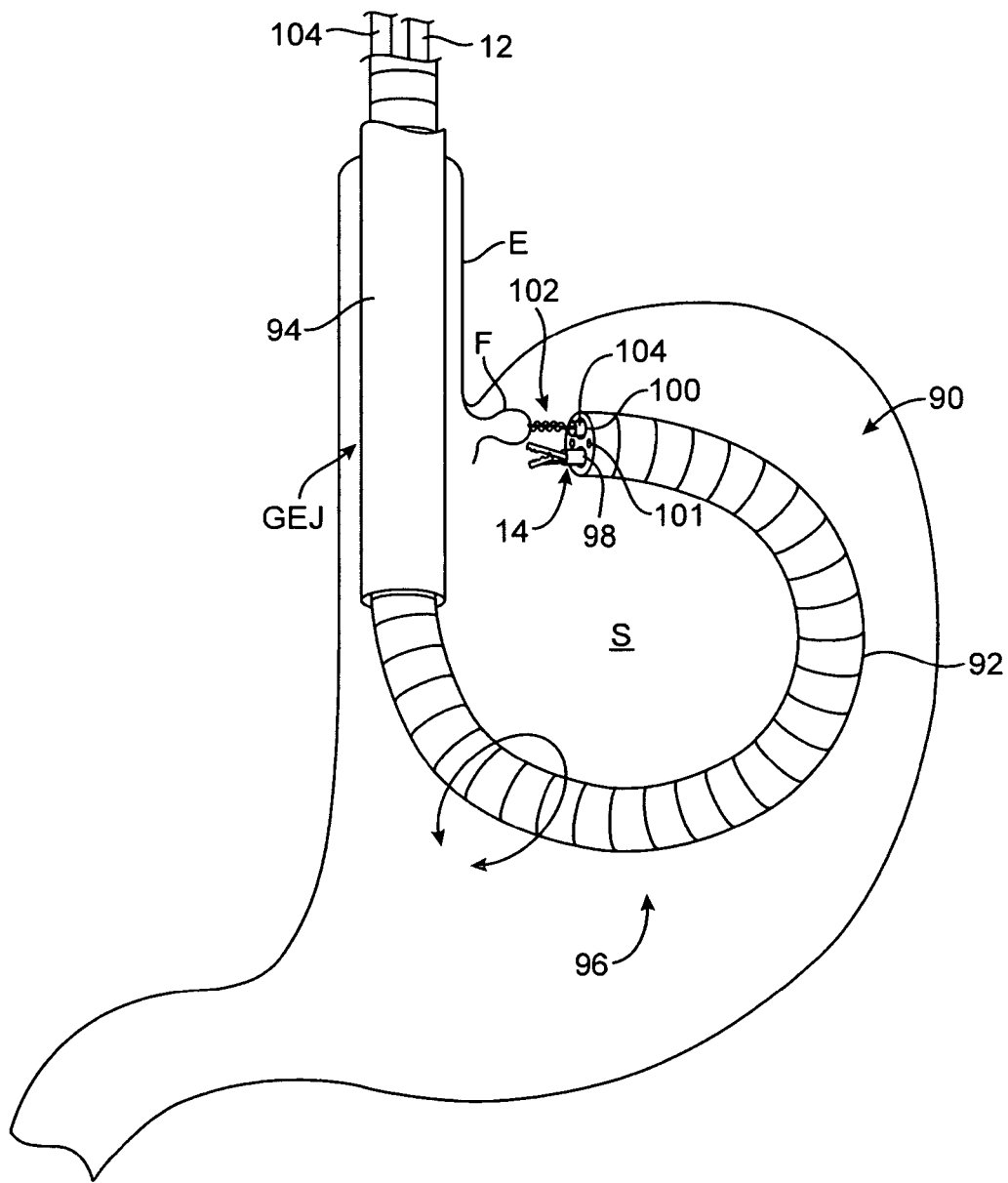
FIG. 6 illustrates one example in which a shape-lockable endoscopic assembly may be advanced into a patient's stomach per-orally and through the esophagus with a tissue manipulation assembly advanced through a first lumen and a tissue engagement member advanced through a second lumen.

As illustrated in FIG. 6, one such example is shown in which a shape-lockable endoscopic assembly 90 may be advanced into a patient's stomach S per-orally and through the esophagus E. Such an endoscopic assembly 90 may generally comprise an endoscopic device which may have a distal portion which may be articulated and steered to position its distal end anywhere within the stomach S. Once desirably configured, assembly 90 may then be locked or rigidized to maintain its shape or configuration to allow for procedures to be performed on the tissue utilizing any number of tools delivered through the assembly 90. Shape-lockable assembly 90 and its variations are described in further detail in U.S. patent application Ser. No. 10/734,562 filed Dec. 12, 2003, which is incorporated herein by reference in its entirety.

Shape-lockable assembly 90 may be generally comprised of shape-lockable endoscopic body 92 having an articulatable distal portion 96. The endoscopic body 92 may define at least first and second lumens 98, 100, respectively, through the endoscopic body 92 through which one or more tools may be deployed into the stomach S. Additional lumens may be provided through shape-lockable endoscopic body 92, such as a visualization lumen 101, through which an endoscope may be positioned to provide visualization of the region of tissue. Alternatively, an imager such as a CCD imager or optical fibers may be provided in lumen 101 to provide visualization. An optional thin wall sheath 94 may be disposed through the patient's mouth, esophagus E, and possibly past the gastroesophageal junction GEJ into the stomach S. Shape-lockable body 92 may be advanced through esophagus E (and through sheath 94, if utilized) and into stomach S while disposed in a flexible state.

Distal steerable portion 96 of endoscopic body 92 may be then articulated to an orientation, e.g., whereby distal portion 96 facilitates engagement of tissue near and/or inferior to the patient's gastroesophageal junction GEJ. Accordingly, distal steerable portion 96 may comprise a number of steering features, as described in further detail in U.S. patent application Ser. No. 10/734,562, incorporated above. With distal steerable portion 96 disposed in a desired configuration or orientation, endoscopic body 92 may be reversibly shape-locked to a rigid state such that the endoscopic body 92 maintains its position within the stomach S. Various methods and apparatus for rigidizing endoscopic body 92 along its length are also described in further detail in U.S. patent application Ser. No. 10/734,562, incorporated above.

FIG. 6 shows tissue manipulation assembly 14 having been advanced through first lumen 98 and a tissue engagement member 102 positioned upon flexible shaft 104 advanced through second lumen 100. As the tissue wall of a body lumen, such as the stomach, typically comprises an inner mucosal layer, connective tissue, the muscularis layer and the serosa layer. To obtain a durable purchase, e.g., in performing a stomach reduction procedure, tissue engagement member 102 may be advanced into contact with the tissue and preferably engages the tissue F such that when the tissue engagement member 102 is pulled proximally to draw the engaged tissue F between the jaw members 20, 22 of tissue manipulation assembly 14, at least the muscularis tissue layer and the serosa layer is drawn into tissue manipulation assembly 14.

Figure 7:
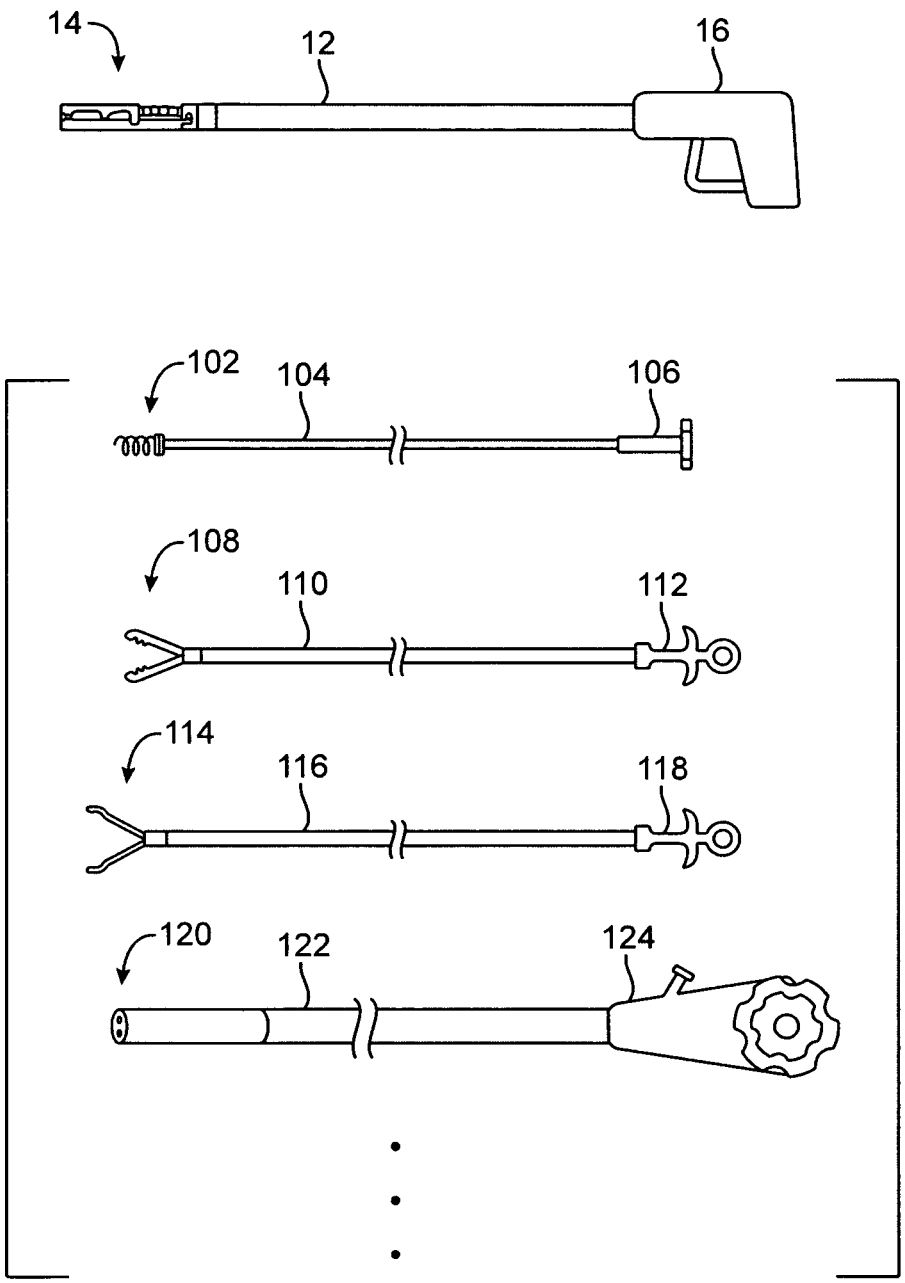
FIG. 7 illustrates a tissue manipulation assembly and examples of various tools which may be used in combination with the tissue manipulation assembly.

As tissue manipulation assembly 14 may be utilized to grasp and secure the engaged tissue, any number of tools may be utilized with tissue manipulation assembly 14, e.g., through shape-lockable endoscopic body 92, to engage and manipulate the tissue of interest relative to tissue manipulation assembly 14. FIG. 7 illustrates tissue manipulation assembly 14 upon flexible body 12 with handle 16 and examples of various tools which may be used in combination with tissue manipulation assembly 14.

Turning to FIG. 7, one example of a tool utilizable in combination with tissue manipulation assembly 14 is shown in tissue engagement member 102 as a tissue piercing helix or corkscrew structure upon flexible shaft 104 (as shown in FIG. 6). Tissue engagement member 102 may be rotated about its longitudinal axis to engage the tissue of interest by rotating handle 106 located on the proximal end of flexible shaft 104. Alternatively, a tool having aggressive tissue graspers 108 positioned upon flexible shaft 110 and articulatable via handle 112 may be utilized in combination with tissue manipulation assembly 14. Another alternative tool may be tissue graspers 114 positioned upon flexible shaft 116 and articulatable via handle 118. Tissue graspers 114 may have atraumatic grasping surfaces. In yet another alternative, an endoscope 122 having optical fibers or imager 120 may be utilized for providing visualization. Endoscope 122 may be articulated via handle 124 at its proximal end.

The examples of the various tools as shown and described are intended merely to be illustrative of the range of tools which may be usable with assembly 14 and are not intended to be limiting in any manner. Any number of other tools may be accordingly utilized and are intended to be within the scope of this disclosure.

Figure 8A:
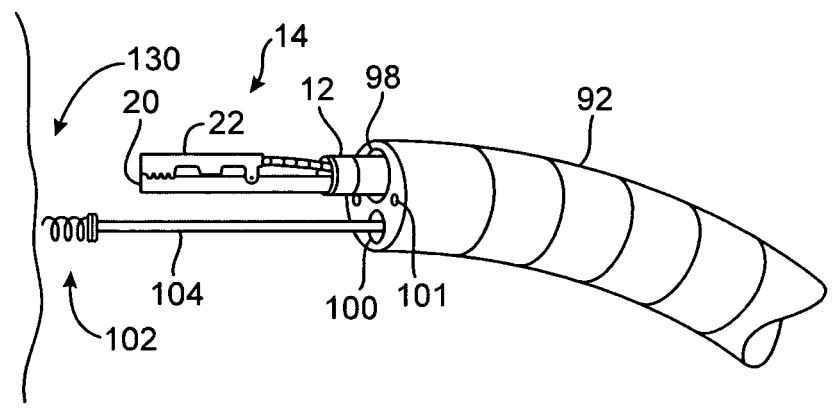
FIGS. 8A to 8D illustrate an example for performing an endoluminal tissue manipulation and securement procedure utilizing a tissue manipulation assembly in combination with a separate tissue grasping tool within, e.g., a patient's stomach.

An example of performing an endoluminal tissue manipulation and securement procedure utilizing tissue manipulation assembly 14 in combination with a separate tissue grasping tool within, e.g., a patient's stomach, is illustrated in FIGS. 8A to 8D. As shown in FIG. 8A, once shape-lockable endoscopic body 92 has been introduced into the patient, e.g., trans-orally, trans-anally, percutaneously, etc., and desirably positioned relative to a tissue region of interest 130, endoscopic body 92 may be rigidized to maintain its configuration within the patient body. Alternatively, it may be left in a flexible state during the procedure.

Figure 8B:
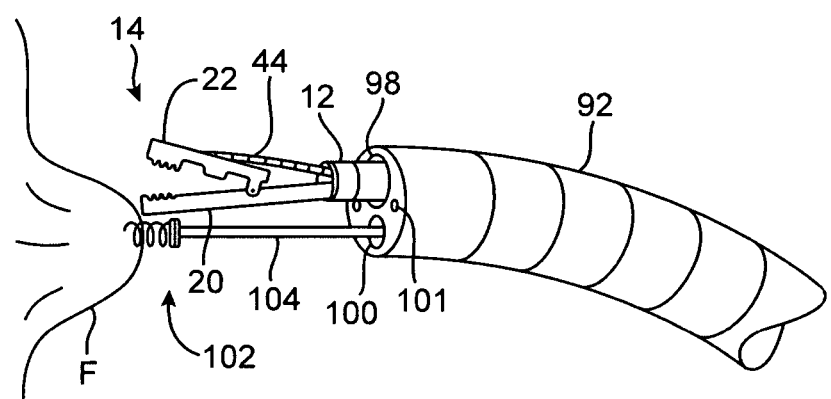

The tissue region of interest 130 as well as the procedure may be visualized through visualization lumen 101 or a separate imager, as described above. In either case, tissue manipulation assembly 14 and tissue engagement member 102 may be advanced distally out from endoscopic body 92 through their respective lumens 98, 100. Tissue engagement member 102 may be advanced into contact against the tissue surface, as shown in FIG. 8A, and then rotated via its proximal handle until the tissue is engaged. The engaged tissue F may be pulled proximally relative to endoscopic body 92 and tissue manipulation assembly 14 may be actuated via its proximally located handle into an open expanded jaw configuration for receiving the engaged tissue F, as shown in FIG. 8B.

Alternatively, once the tissue F has been engaged, tissue manipulation assembly 14 may be advanced distally in its open configuration onto the engaged tissue. In yet another variation, tissue engagement member 102 may be omitted entirely and tissue manipulation assembly 14 may be utilized alone to grasp onto the tissue region of interest 130. In yet another alternative, a second tissue manipulation assembly may be used in combination with tissue manipulation assembly 14.

Figure 8C:
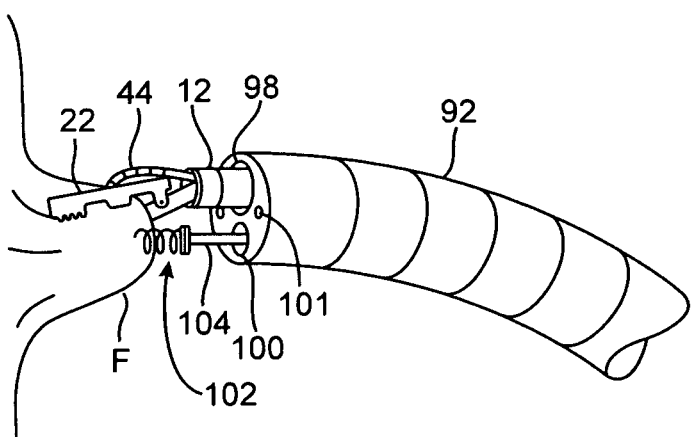

Turning back to FIG. 8B, tissue manipulation assembly 14 may be articulated to receive the engaged tissue F. As shown in FIG. 8C, once engaged tissue F is positioned between jaw members 20, 22, the launch tube may be urged proximally to actuate upper jaw member 22 to grasp or clamp upon the tissue F. Tissue engagement member 102 may be retracted from the tissue F or it may be left within the tissue while tissue manipulation assembly engages and secures the tissue F.

Figure 8D:
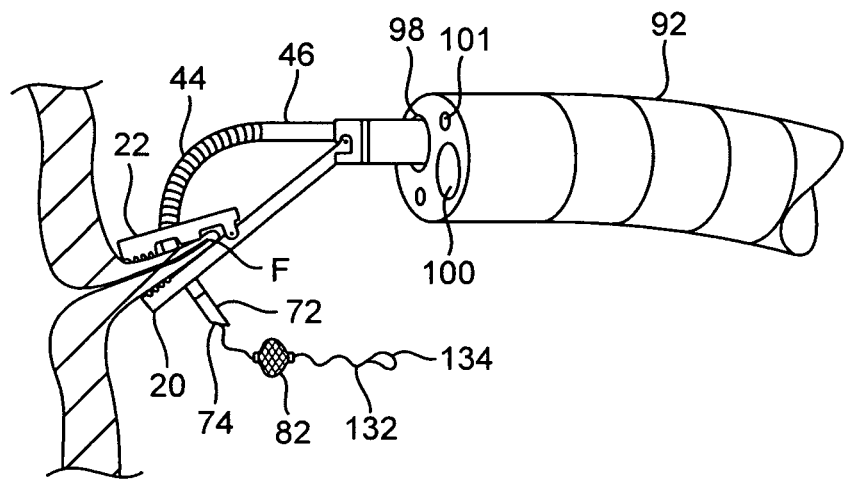

FIG. 8D shows a partial cross-sectional view of the tissue F while engaged to tissue manipulation assembly 14. Tissue engagement member 102 has been omitted from this view only for the sake of clarity. As mentioned above, member 102 may be left remaining in the tissue F, disengaged from tissue F, or disengaged and removed entirely from endoscopic body 92, if so desired, and another tool may be advanced through lumen 100 to facilitate the procedure. Once jaw members 20, 22 have been actuated to clamp or grasp upon tissue F by the launch tube, the launch tube may be automatically positioned into its anchor deployment configuration. The needle assembly may then be urged via manipulation from its proximal end at handle 16 through the launch tube to pierce preferably through a dual serosa layer through engaged tissue F and past lower jaw member 20. As described above, the engaged tissue F positioned between the jaw members 20, 22 is desirably engaged such that the needle body 72, when urged through the tissue F, is disposed through the muscularis and/or serosa layers of the engaged tissue F. Once needle body 72 has passed through tissue F, one or more expandable tissue anchors may be ejected from needle body 72 through needle opening 74.

Because needle body 72 may penetrate the tissue wall twice, it exits within the body lumen if utilized within, e.g., the stomach, thus reducing the potential for injury to surrounding organs. As described above, needle body 72 may define needle lumen or opening 74 through which an expandable anchor, e.g., distal anchor 82 and/or proximal anchor 84, may be situated during deployment and positioning of the assembly. A single suture or flexible element 132 (or multiple suture elements) may connect distal anchor 82 and proximal anchor 84 to one another and end in terminal loop 134. For instance, element 132 may comprise various materials such as monofilament, multifilament, or any other conventional suture material, elastic or elastomeric materials, e.g., rubber, etc.

Once distal anchor 82 has been ejected, needle body 72 may be urged proximally back through tissue F, where proximal anchor 84 may then be ejected from needle body 72 with suture 132 still connecting the two anchors 82, 84 through tissue F. Alternatively, tissue manipulation assembly 14, with suture 132 still depending therefrom, may be disengaged from tissue F and the procedure may be repeated at a second region of tissue where proximal anchor 84 may then be ejected.

Figure 9A:
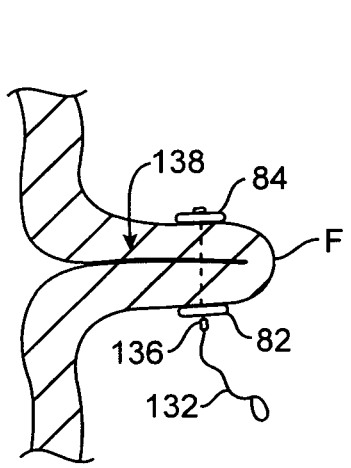
FIG. 9A shows one variation where a single tissue fold may be secured between tissue anchors using the tissue manipulation assembly.

FIG. 9A shows one variation where a single fold F may be secured between proximal anchor 82 and distal anchor 84. With both anchors 82, 84 disposed externally of the launch tube and suture 132 connecting the two, proximal anchor 84 may be urged into contact against tissue F. As the anchors are urged against tissue fold F, distal anchor 82 or a portion of suture 132 may be configured to provide any number of directionally translatable locking mechanisms 136 which provide for movement of an anchor along suture 132 in a first direction and preferably locks, inhibits, or prevents the reverse movement of the anchor back along suture 132.

Figure 9B:
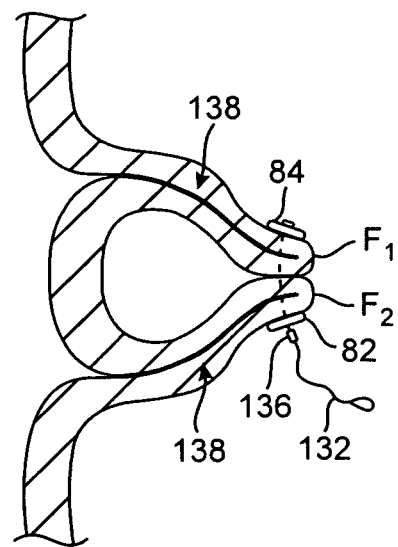
FIG. 9B shows another variation where two or more tissue folds may be secured between tissue anchors using the tissue manipulation assembly.

FIG. 9B shows another variation where a at least two folds $F_1$ and $F_2$ may be secured between proximal anchor 82 and distal anchor 84. After the anchors have been ejected from needle body 72, the anchors may be approximated towards one another over suture 132 thus bringing folds $F_1$ and $F_2$ towards one another. Although a single tissue fold and a dual fold are shown in these examples, any number of folds or tissue ridges may be created using the tools disclosed herein. Moreover, these examples are merely intended to be illustrative and not limiting in any way. In either case, it may be generally desirable to form the tissue folds such that serosa-to-serosa contact 138 occurs between the layers of secured tissue, although this may not be necessary.

Various examples of cinching devices and methods which may be utilized with the tools and devices herein are described in further detail in U.S. patent application Ser. No. 10/840,950 filed May 7, 2004, which has been incorporated herein above.

Figure 10A:
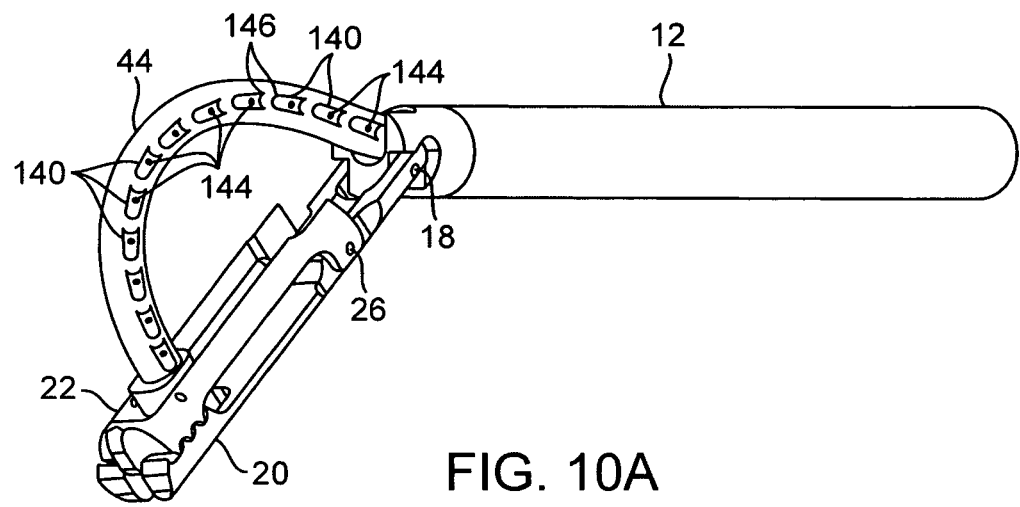
FIGS. 10A and 10B illustrate a variation of the tissue manipulation assembly in a perspective and cross-sectional view, respectively, where a number of reinforcement members or bars may be positioned along the launch tube to increase its column strength.
Figure 10B:
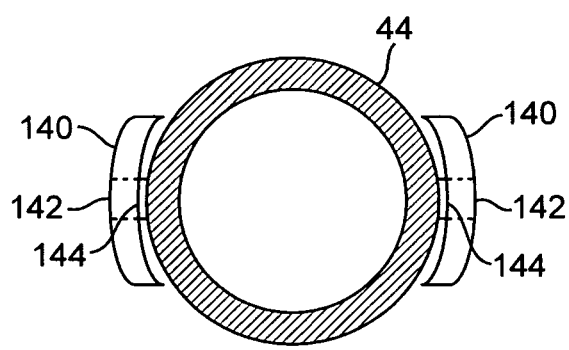

In using the launch tube as a jaw actuation mechanism, other variations of the launch tube may be utilized to ensure sufficient strength and force transmission in tissue manipulation assembly 14 for jaw member actuation. One such example is shown in the perspective view of FIG. 10A, which shows launch tube 44 having a number of reinforcement members or bars 140 aligned along one or both sides of the launch tube to provide for additional column strength. Each of the reinforcement members 140 may be pivotally attached to launch tube 44 via pivot members 144 rotatably secured within pivot channels 142, as seen in the launch tube cross-section in FIG. 10B. Moreover, each of the pivot members 144 may define cooperating adjacent members relative to one another while maintaining contact to allow for the transmission of force between the members 144. Pivot members 144 may be positioned along the length of the exposed launch tube or a portion of the launch tube; moreover, a single side of the launch tube may have pivot members 144 attached thereto. Alternatively, rather than utilizing pivot members, portions of the launch tube itself may be simply thickened to increase its column strength and force transmission capabilities.

Figure 11A:
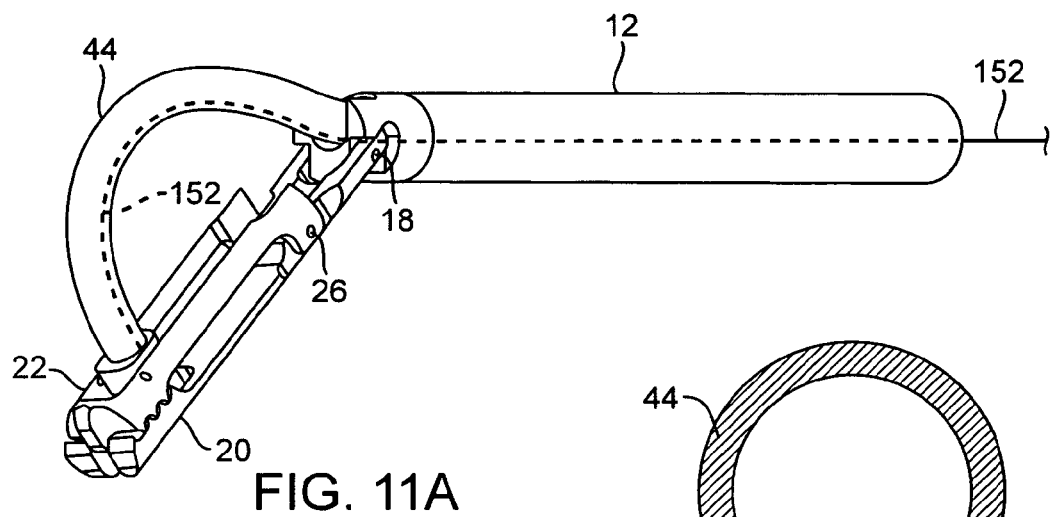
FIGS. 11A and 11B illustrate another variation of the tissue manipulation assembly in a perspective and cross-sectional view, respectively, where a pull wire may be routed through the launch tube to facilitate articulation of the launch tube and/or jaw assembly.
Figure 11B:
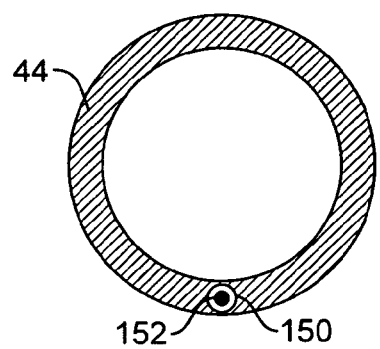
Figure 12:
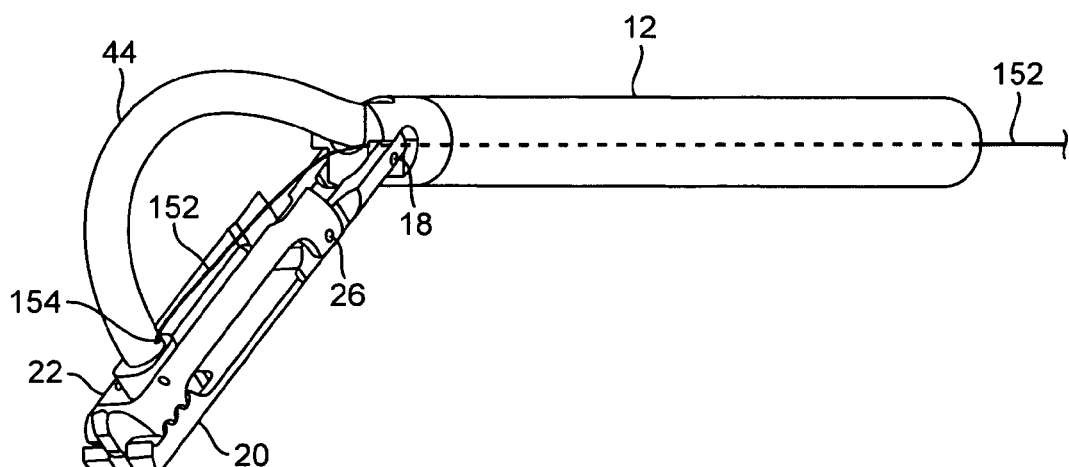
FIG. 12 illustrates yet another variation of the tissue manipulation assembly which may also utilize a pull wire connected directly to the launch tube.

In another variation, as shown in FIG. 11A and the launch tube cross-section in FIG. 11B, a pull wire 152 may be routed through tubular body 12 and launch tube 44 through a pull wire lumen 150 to provide a launch tube and jaw actuation mechanism separate from the launch tube actuation itself. Pull wire 152 may be manipulated via its proximal end at handle 16 by pulling or pushing pull wire 152 to actuate launch tube 44 and/or jaw members 20, 22. Alternatively, as seen in FIG. 12, pull wire 152 may be routed through tubular body 12 and connected directly to launch tube 44 at pull wire attachment point 154 rather than routing it through the launch tube. Again, manipulation of pull wire 152 may be utilized to articulate the launch tube configuration as well as jaw member articulation.

Referring now to FIGS. 13 and 14, a variation of the anchor assembly and the needle deployment assembly is described. As with previously described needle deployment assembly 60, assembly 60' comprises needle assembly control or housing 62, tubular sheath 64 and needle assembly 66 having needle body 72 with opening 74. Elongate pusher 76 is configured for translation within sheath 64 via actuation member 78. Pusher 76 illustratively comprises a hypotube having lumen 77 defined therethrough.

In the variation of FIGS. 13 and 14, locking mechanism 136 of anchor assembly 68' is disposed proximal of proximal anchor 84, and the anchor assembly is positioned within the distal portion of tubular sheath 64, such that the distal region of pusher 76 abuts locking mechanism 136. Suture or flexible element 132' comprising distal knot or protrusion 133 extends proximally from the knot in a manner that connects distal anchor 82, proximal anchor 84 and locking mechanism 136. Element 132' then further extends through lumen 77 of pusher 76 to a proximal region of assembly 60' such that element 132' may be manipulated by a medical practitioner from outside a patient. The medical practitioner may, for example, engage previously described suture loop 134, or may engage some other control element 134', such as a ring or handle, disposed at the proximal end of suture element 132'. As will be apparent, in another variation, element 132' may extend to the proximal region of assembly 60' alongside pusher 76 rather than within a lumen of the pusher.

With reference to FIG. 15, a method of using anchor assembly 68' and needle deployment assembly 60' is described. For the purposes of illustration, the assemblies are shown securing tissue without use of a tissue manipulation assembly. However, it should be understood that the assemblies alternatively may be used in combination with a tissue manipulation assembly, such as previously described tissue manipulation assembly 14 of assembly 10.

Figure 15A:
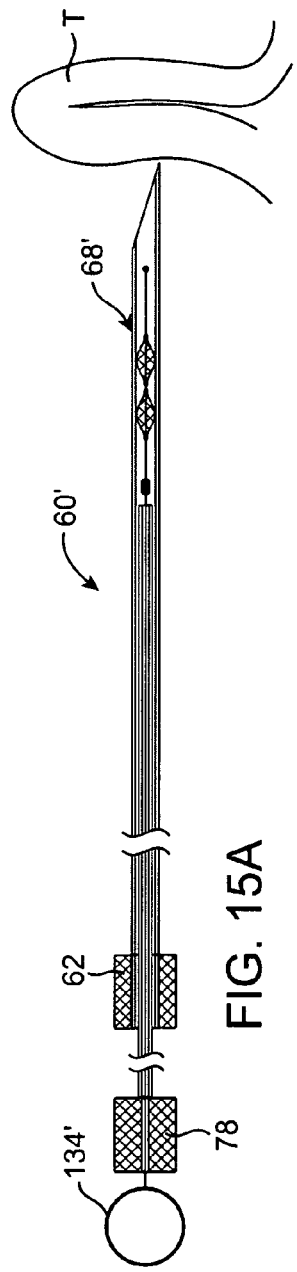
FIGS. 15A to 15F illustrate an exemplary method of using the anchor assembly and needle deployment assembly variation of FIGS. 13 and 14.
Figure 15B:
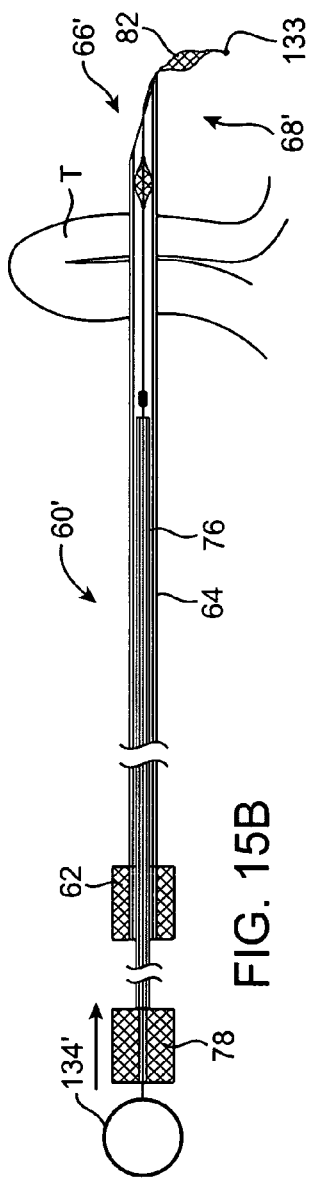
Figure 15C:
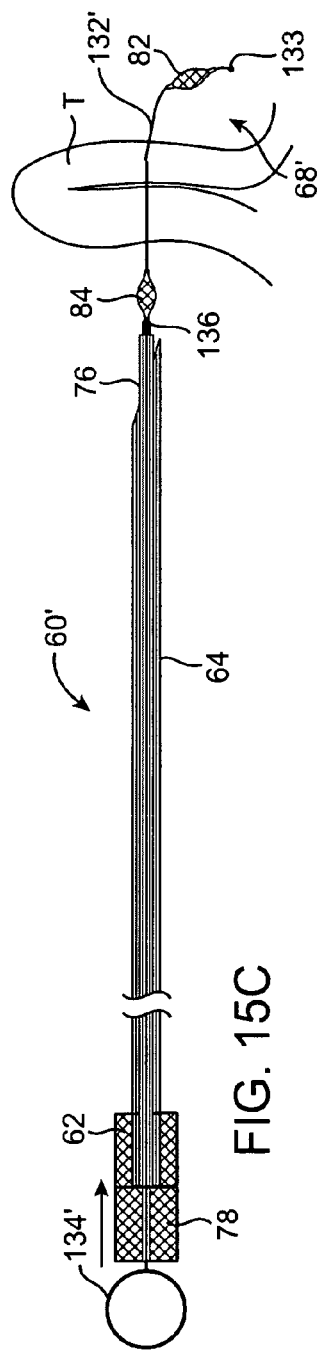

In FIG. 15A, needle deployment assembly 60' has been positioned in proximity to approximated tissue T. The assembly is advanced such that needle assembly 66 pierces the tissue and is advanced through and across the tissue, as in FIG. 15B. Pusher 76 is advanced within the lumen of sheath 64 via actuation member 78, such that distal anchor 82 of anchor assembly 68' is ejected through opening 74 of needle body 72 of needle assembly 66 on the distal side of approximated tissue T. Needle deployment assembly 60' and pusher 76 then are retracted such that the pusher and needle assembly 66 again are disposed on the proximal side of the approximated tissue, as in FIG. 15C. Next, pusher 76 is distally advanced relative to sheath 64 to eject proximal anchor 84 from the sheath.

Figure 15D:
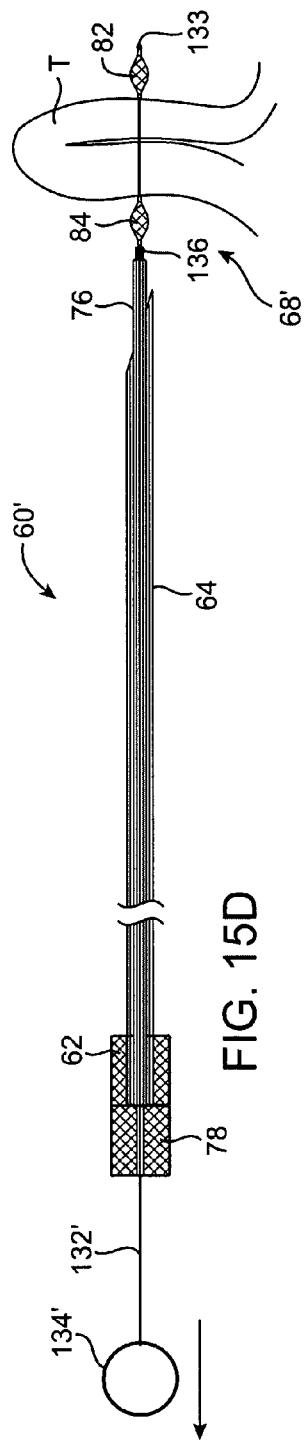

In FIG. 15D, with the proximal and distal anchors of anchor assembly 68' disposed on either side of the approximated tissue, the anchor assembly is cinched by retracting control element 134' relative to needle deployment assembly 60'. Pusher 76 abuts locking mechanism 136 and urges it distally during proximal retraction of element 134', which shortens the length of suture element 132' disposed between distal anchor 82 and proximal anchor 84, thereby cinching anchor assembly 68'. Locking mechanism 136 ensures that the anchors remain cinched by resisting distal passage of element 132' through the mechanism, thereby resisting subsequent separation of the proximal and distal anchors.

Figure 15E:
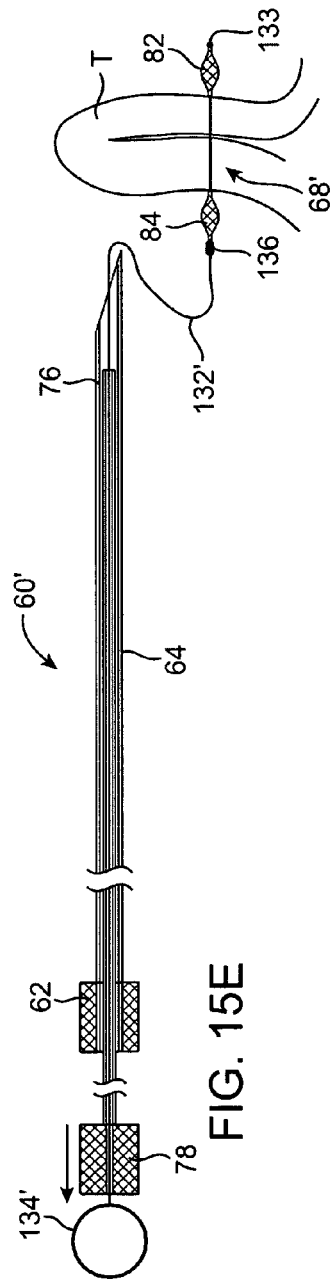
Figure 15F:
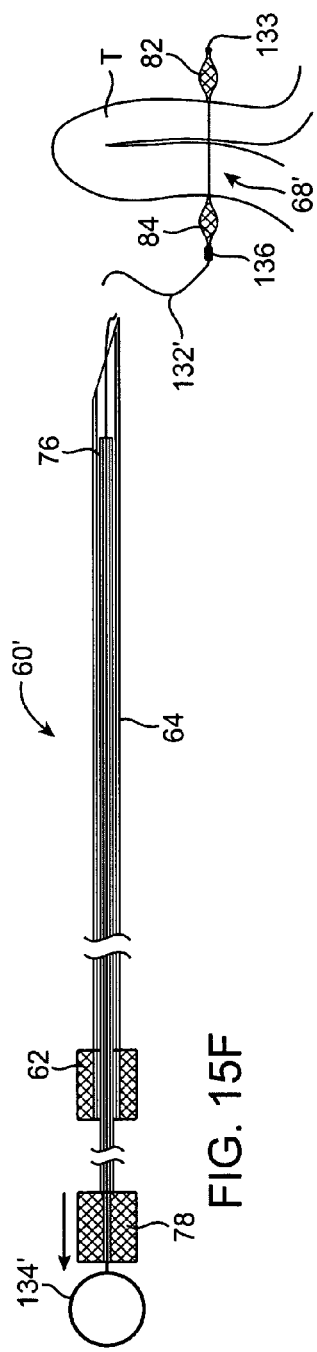

With anchor assembly 68' cinched, pusher 76 is retracted relative to sheath 64 such that needle assembly 66 engages suture element 132', as in FIG. 15E. The needle assembly cuts the suture proximal of locking mechanism 136, as in FIG. 15F. The medical practitioner may facilitate cutting of the suture element by manipulating control element 134' of anchor assembly 68' and/or by manipulating needle assembly control 62 of needle deployment assembly 60'.

Referring now to FIG. 16, a variation of the suture element of anchor assembly 68' is described. In FIG. 16, suture element 132" comprises segment 135 of reduced integrity. The segment may for example, comprise fewer suture strands or may be reduced in integrity via chemical, electrical, thermal or physical processing, etc. Segment 135 may locally reduce the tensile strength of element 132" to a desired threshold. When used to cinch anchor assembly 68' in combination with anchor deployment assembly 60', the segment may obviate a need to cut the suture with needle assembly 66 after cinching of the anchor assembly. Specifically, the anchor assembly may be cinched to a desired tension after which segment 135 plastically deforms and snaps, leaving the anchor assembly cinched and in place.

With reference to FIG. 17, a variation of the needle assembly of needle deployment assembly 60' is described. Needle body 72' of needle assembly 66' may comprise one or more recessed cut-outs 73 having sharpened edges E for cutting the suture element. After cinching of anchor assembly 68', the suture element may be snagged within a cut-out 73 and cut by the sharpened edge of the cut-out.

Referring now to FIG. 18, alternative control mechanisms for needle deployment assembly 60' are described. Actuation member 78' for controlling pusher 76 may be integrated with needle assembly control 62', such that the actuation member is advanceable in controlled increments relative to the needle assembly control via detents 63 of the needle assembly control that coact with actuation member 78'.

With reference to FIG. 19, another variation of the anchor assembly and needle deployment assembly is shown. Control element 134' of anchor assembly 68' is coupled to or abuts needle assembly control 62' of needle deployment assembly 60'. When distal anchor 82 of anchor assembly 68' is disposed on the distal side of approximated tissue T, as in FIG. 19A, the proximal and distal ends of suture element 132' are constrained. Thus, as seen in FIGS. 19A and 19B, advancement of pusher 76 via actuation member 78' advances both proximal anchor 84 and locking mechanism 136 of anchor assembly 68'. This causes the anchor assembly to be progressively cinched as the proximal anchor is advanced. Once the anchor assembly has been ejected from sheath 64, as in FIG. 19B, and adequately cinched, as in FIG. 19C, suture element 132' may be cut proximal of the locking mechanism, e.g., with needle assembly 66 as described previously.

Referring to FIG. 20, a variation of the needle deployment assembly is described. Pusher 76' comprises suture ports 79 through which suture element 132 of anchor assembly 68' is routed. As seen in FIG. 20A, with pusher 76' disposed within tubular sheath 64 of needle deployment assembly 60', suture element 132' passes out of the pusher between the suture ports and is disposed between the pusher and the interior wall of the tubular sheath. As seen in FIG. 20B, when pusher 76' is advanced through and distal of needle assembly 66, e.g., to eject proximal anchor 84 of anchor assembly 68' from the needle deployment assembly and/or to cinch the anchor assembly, the section of suture element 132' between the suture ports is exposed. Subsequent retraction of the pusher relative to the needle assembly causes the section of exposed suture to contact the sharpened edge of needle assembly 66, thereby severing suture element 132' as in FIG. 20C.

Turning now to FIG. 21, another variation of the needle deployment assembly is shown. In this variation, suture element 132'" may form a terminal loop 158 through which a release suture or wire 156 may be passed. Release suture or wire 156 may be routed through the length of the needle deployment assembly and through pusher 76, as described above, and both release suture or wire 156 and terminal loop 158 may both be situated within pusher 76, as shown in FIG. 21A. After deployment of the anchors into tissue and cinching of the assembly, as described above, one end of release suture or wire 76 may be pulled or tensioned proximally in the direction shown by arrow 162, as in FIG. 21B. This pulling may draw a terminal end of release suture or wire 156 through pusher 76 until terminal loop 158 of suture element 132'" has been released therefrom, as shown in FIG. 21C.

In yet another variation shown in FIG. 22A, terminal loop 158 of suture element 132'" may be seen restrained within pusher 76 via reconfigurable hook 164 of release wire 156'. Here, release wire 156' may be fabricated from a shape memory or superelastic alloy material, such as Nitinol, which has been preformed to reconfigure its terminal end from a hook 164 configuration to a straightened or opened configuration once released from the constraints of pusher 76. Thus, after deployment and cinching of the anchor assembly, release wire 156' may be advanced distally through pusher 76, as shown in FIG. 22B, until reconfigurable hook 164, which is retained in a hooked or obstructive configuration within the lumen of pusher 76, has been advanced out of pusher 76. Once free from the constraints of the lumen, hook 164 may reconfigure itself into an opened or straightened configuration to thereby release terminal loop 158 of suture element 132'", as shown in FIG. 22C. Hook 164 having released terminal loop 158, may then be withdrawn proximally back into pusher 76 in its straightened configuration.

In another variation shown in FIG. 23A, a terminal end of suture element 132'" may have an obstructive or enlarged element 160, e.g., a knot, formed thereon. The terminal end of suture element 132'" with obstructive element 160 may be looped around release suture or wire 156 and retained within the lumen of pusher 76. After anchor deployment and cinching, release suture or wire 156 may be drawn distally with looped obstructive element 160 retained securely thereto, as shown in FIG. 23B, until obstructive element 160 and release suture or wire 156 have been advanced out of pusher 76. Once free from the constraints of the pusher lumen, obstructive element 160 may be released from release suture or wire 156, as shown in FIG. 23C, to thus release suture element 132'''.

Turning now to the alternative variation shown in FIGS. 24A to 24C, suture element 132' may be passed through pusher 76" having heating element assembly 170 disposed upon the distal end of pusher 76". Heating element assembly 170 may generally comprise a heating element 172, e.g., a resistive metallic conductor such as nichrome, and an insulating element 174 disposed distally of heating element 172, as shown in FIG. 24A. In use, pusher 76" may be urged distally from needle assembly 66 to cinch the anchors against the tissue surface, as described above. With heating element assembly 170 disposed externally or internally of needle assembly 66, heating element 172 may be powered such that its increase in temperature surpasses the melting point of the suture element 132' passing therethrough, as shown in FIG. 24B. The melting point of the suture 132' will vary depending upon the type of suture utilized.

Insulating element 174, which may be made from any number of electrically and thermally non-conductive insulating materials such as ceramics, polyimides, etc., may be disposed distal of heating element 172 to prevent inadvertent contact against the tissue by heating element 172 while it is heated although insulating element 174 may be omitted entirely from the assembly 170. As heating element 172 is heated, the portion of suture 132' adjacent to element 172 will be melted and subsequently cut forming melted suture ends 176, 176' on their respective terminal ends of suture element 132' and the remaining suture length 178, as shown in FIG. 24C.

FIG. 25A shows a partial cross-sectional detail view of the heating element assembly 172 disposed upon the distal end of pusher 76". As shown, heating element 172 and insulating element 174 may be positioned adjacent to one another. A covering, coating, or insulating layer 180 (e.g., heatshrink made from FEP, PEEK, Teflon, polyimide, etc.) may be disposed over the heating assembly 170 entirely or at least partially such that heating element 172 is completely encapsulated and insulated from surrounding tissue except for the inner exposed surface within lumen 188, where it may come in contact with or in proximity to the suture for severing the suture element 132'. Electrically conductive wires 182, which may be embedded along the length of pusher 76", may be routed through heating element assembly 170 via wire contact lumens 184, 186 to not only provide power to heating element 172, but also to provide structural support in maintaining the position of heating element assembly 170 upon the distal end of pusher 76". Alternatively, the elements 172, 174 of assembly 170 may be attached to one another utilizing any number of mechanical fasteners, e.g., adhesives, threaded connections, interference fitting, etc.

FIG. 25B shows a partial assembly of pusher 76" and elements 172, 174 in an exploded view (cover 180 has been omitted for clarity). Wires 182 may pass through heating element assembly 170, along pusher 76", and proximally into electrical contact with a controller and/or power supply 190 via a standard removable connector or through a direct electrical connection. Controller/power supply 190 may be located externally of the patient as a device separate from pusher 76" and within or outside a sterile surgical field around the patient. Alternatively, the power supply 190 may be integrated with a proximal portion of the pusher 76". An actuator 192, such as a foot-operated pedal or hand-operated switch, may be electrically connected via connector 194 to controller/power supply 190 for controlling the actuation of the heating element assembly 170.

An alternative heating assembly is shown in FIGS. 26A and 26B. FIG. 26A illustrates a partial side view of pusher 76''' having a heating assembly 200 disposed upon the distal end of pusher 76''' with suture element 132' routed therethrough. Heating assembly 200 may generally comprise an insulative body 202 having a circumferentially-defined depression 204. One or more slots, grooves, or openings 206 extending radially through body 202 may be defined within the depression 204 such that an electrically resistive wire 208 which is coiled, wrapped, or otherwise wound around body 202 along depression 204 may effectively transfer heat generated by wire 208 through the one or more openings 206 to melt and separate the portion of suture element 132' positioned within lumen 210 of body 202, as shown in FIG. 26B. A portion of coiled wire 208 may be optionally potted with an insulating material, such as epoxy, within depression 204 to retain the wire 208 in place as well as to insulate the wire 208 from surrounding tissue.

The heating assembly 200 may be positioned upon the distal end of pusher 76''' utilizing any of the methods described above or generally known. Moreover, conductive wires 182 may be routed along or through pusher 76''' and connected via, e.g., a connector, to controller and/or power supply 190, which may be connected to a foot pedal, hand switch, or other actuator 192, as described above.

Yet another variation is shown in the partial cross-sectional view of pusher 76'''' of FIG. 27A, which shows an alternative heating assembly 220 having a resistive wire or element 224 encased within a casing or housing 222 which forms a portion of the pusher wall.

Although the housing 222 is shown near or at the distal end of pusher 76'''', housing 222 may also be located along the pusher wall proximal to the distal end. FIG. 27B shows a cross-section of a portion of pusher 76'''' and housing 222. As shown, resistive wire 224 may be positioned through housing 222 such that heat from the wire 224 may melt or sever the portion of suture 132' adjacent to or in contact with housing 222. As above, wire 224 may be connected to a proximally located controller/power supply 190.

In the variations described above utilizing a heating element to sever the suture, the heating elements may be powered in a continuous manner until shut off by the user.

Alternatively, the power may be configured to operate for a pre-determined period of time once turned on before automatically shutting off. In yet another alternative, the power may pulse in a cyclical manner such that the heating element is heated only for a specified period of time before automatically shutting off for a set period. This cycle may be repeated until the device is turned off. Such features may be incorporated as part of the instrument as a fail-safe feature, is so desired.

Figure 28:
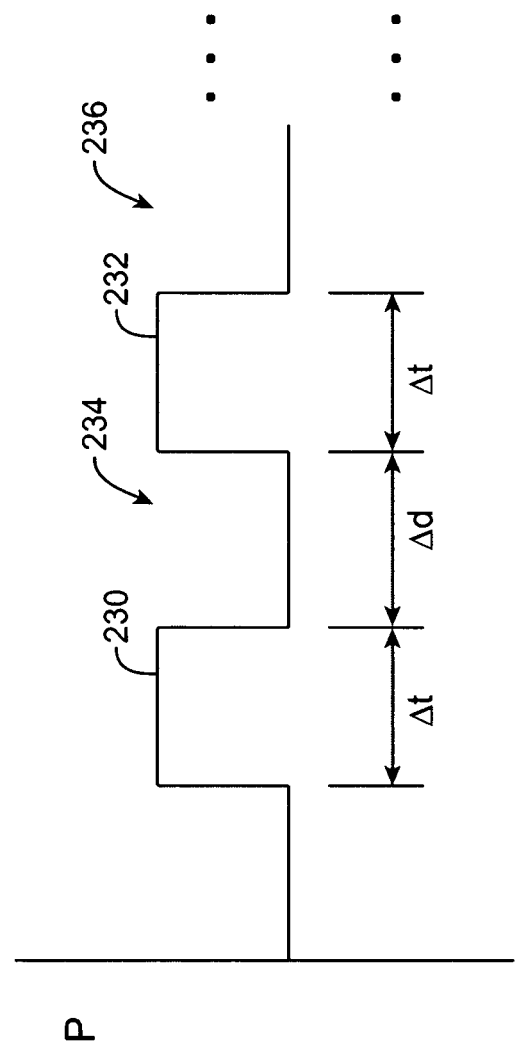
FIG. 28 shows an example of a cyclical timing profile for heating the thermal element.

In one example of a cyclical timing profile shown in FIG. 28, once the actuator has been turned on to heat the heating element to sever the suture, the controller connected to the heating element may be configured to pulse the power 230 for a set period of time, $\Delta t$, e.g., 1 to 2 seconds. The power may then automatically shut off 234 for a set period of time, $\Delta d$, e.g., 1 to 5 seconds; then the power may be automatically turned on again 232 and then off again 236. This may occur for a set number of cycles or for a set period of time before the device is completely shut off or until the user completely shuts the power off upon suture separation.

In yet another variation for effecting suture separation, an alternative pusher 240 is shown in cross-section in FIG. 29A.

Here, pusher 240 may have a needle body 242 with a circumferential cutting edge 244 defined at its distal end, similar to a coring needle, and a lumen 246 defined therethrough for passage of suture element 132'. Once the tissue anchors have been deployed into the tissue, cutting edge 244 may be used to cut or sever suture element 132' passing through pusher 240 and needle body 242. During tissue anchor cinching of the locking mechanism 136 against the tissue anchor, as described above, cutting edge 244 may be optionally tapered to otherwise sized, without obstructing lumen 246, to allow cutting edge 244 to become seated within the locking mechanism 136. Thus, as pusher 240 and needle body 242 abuts against locking mechanism 136 to urge it distally along suture element 132', cutting edge 244 may avoid direct contact against locking mechanism 136 so as to prevent dulling of cutting edge 244.

Alternatively or additionally, locking mechanism 136 itself may be coated or otherwise covered with a heatshrink material or other soft polymeric material, at least over a proximal portion, so as to present an atraumatic surface to cutting edge 244. In a further alternative, an intermediate element (not shown) made of a suitably soft material, e.g., polymers, may be disposed between needle body 242 and locking mechanism 136 to function as a temporary bumper.

Figure 30A:
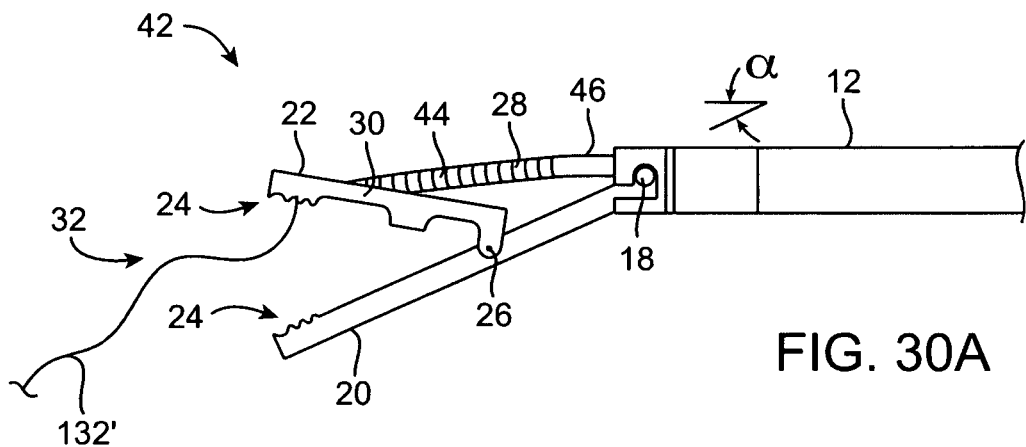
FIGS. 30A to 30C illustrate an alternative method for severing the suture utilizing the tissue manipulation assembly.
Figure 30B:
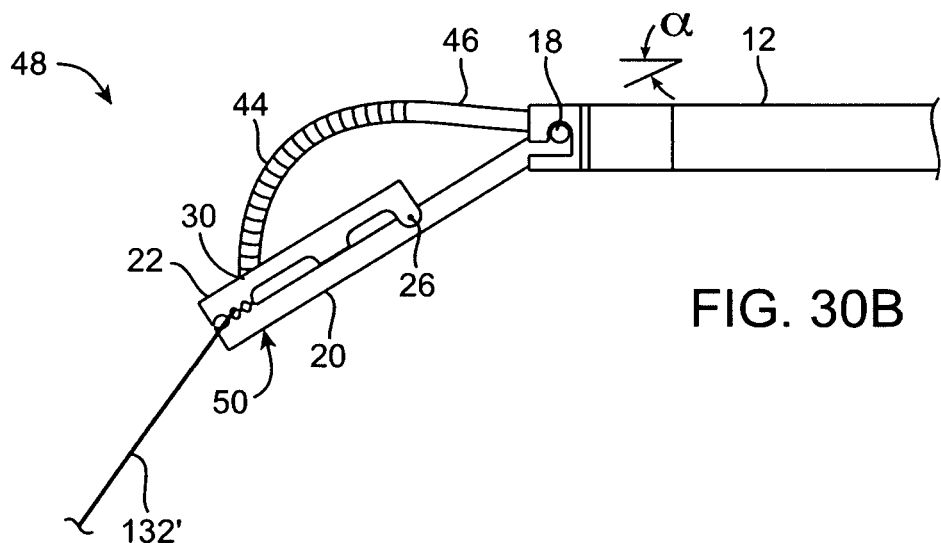
Figure 30C:
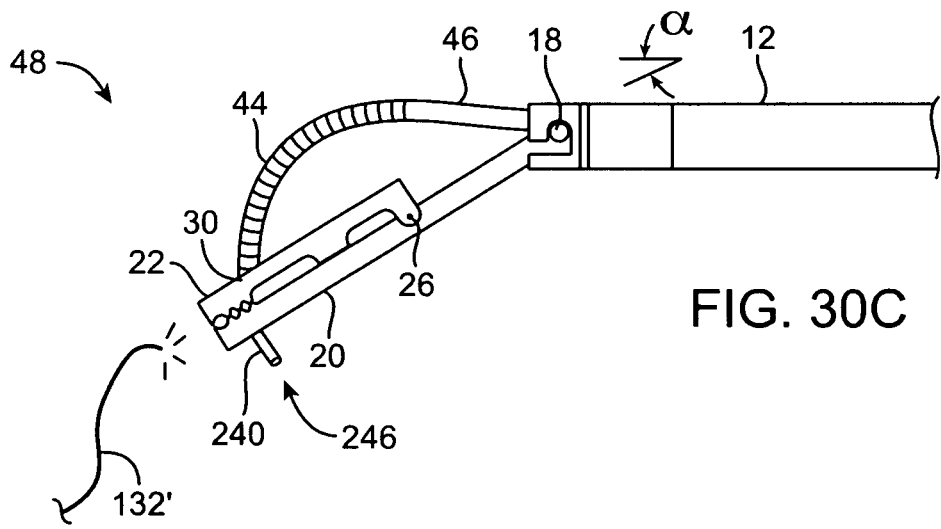

In use, once the tissue anchors and locking mechanism 136 have been desirably deployed, pusher 240 and needle body 242 may be extended and the suture element 132' passing through needle body 242 may be simply severed by pulling or urging suture element 132' against cutting edge 244 until separation occurs. In another alternative method for separating suture element 132', FIGS. 30A to 30C illustrate another method utilizing the tissue manipulation assembly described above. Once the tissue anchors and locking mechanism have been deployed from pusher 240 and launch tube 28, as shown in FIG. 30A, lower jaw 20 and upper jaw 22 of the tissue manipulation assembly may be actuated to clamp upon suture element 132', as shown in FIG. 30B.

The suture element 132' still disposed through pusher 240, which is positioned within the launch tube, may be tensioned at least partially, e.g., by pulling on a proximal end of suture element 132'. With suture element 132' tightly secured between jaw members 20, 22, pusher 240 and needle body 242 may be urged distally through launch tube 28 until cutting edge 244 severs the portion of suture element 132' held tightly by jaw members 20, 22, as shown in FIG. 30C. The tissue manipulation assembly may then be removed from the patient or manipulated to another portion of the body for treatment.

Figure 31A:
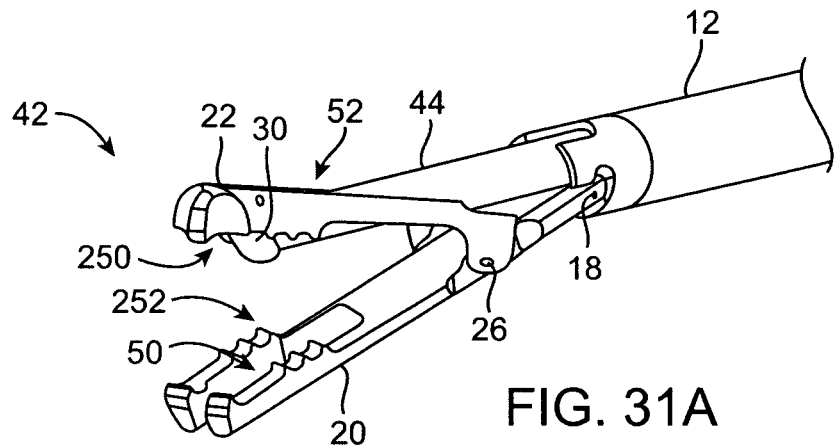
FIGS. 31A to 31E illustrate examples for incorporating a cutting blade or element along regions of the tissue manipulation assembly.
Figure 31B:
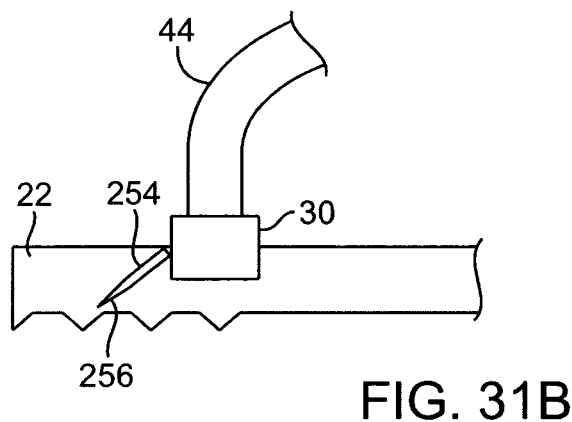
Figure 31C:
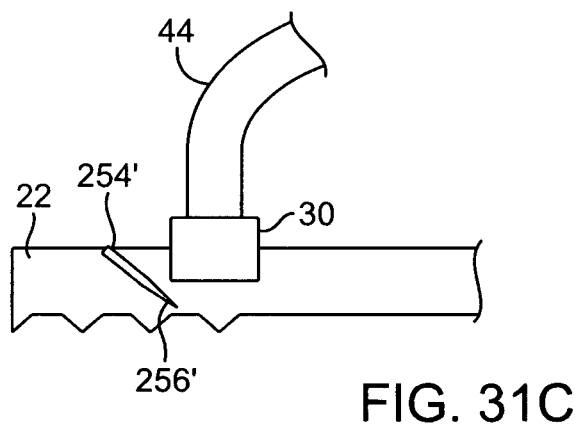

In yet another variation for suture separation, the tissue manipulation assembly may again be utilized by incorporating a suture cutting element along either or both jaw members 20, 22. For example, as shown in FIG. 31A, a cutting element, e.g., a blade, energizable wire, etc., may be positioned along an upper region 250 of upper jaw 22, or a cutting element may be positioned along a lower region 252 of lower jaw 20, or both may be utilized in combination with one another. FIGS. 31B and 31C show partial side views of upper jaw 22 and deployed launch tube 44 and pivot 30. A cutting blade, for instance, may be positioned adjacent to the launch tube 44 and angled at various directions relative to where the suture exits the launch tube such that the blade does not obstruct deployment of the tissue anchors or suture.

Placement of the cutting blade, however, is such that the upper jaw 22 may be manipulated to bring the suture element into contact with the blade for severing the suture. FIG. 31B shows blade 254 angled such that cutting edge 256 is directed away from the launch tube 44 opening. Alternatively, blade 154', in FIG. 31C, shows another example where blade 254' may be angled such that cutting edge 256' is directed towards the launch tube 44 opening.

Figure 31D:
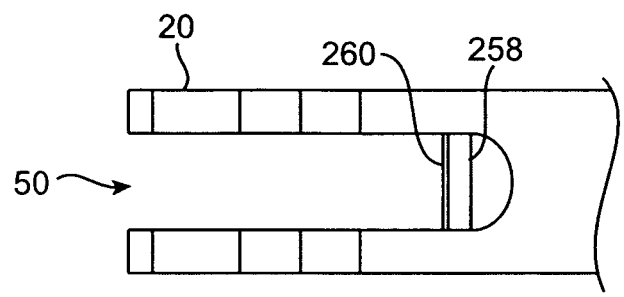
Figure 31E:
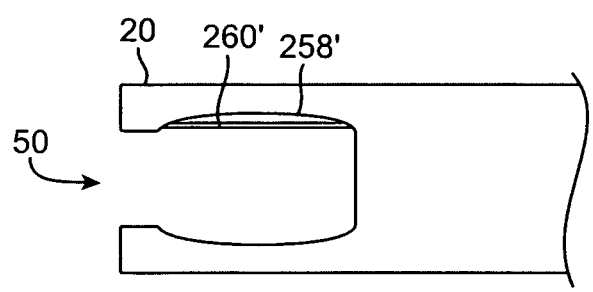

Rather than integrating a cutting blade along upper jaw 22, one or more cutting blades may instead be incorporated along lower jaw 20. As shown in the example of FIG. 31D, a partial top view of lower jaw 20 is shown with an optional cutting blade 258 with cutting edge 260 integrated near a proximal portion of needle assembly opening 50 defined in lower jaw member 20. Another alternative is shown in FIG. 31E where a cutting blade 258' having a cutting edge 260' may be integrated along a side portion of opening 50. These examples shown are intended to be illustrative and not limited and one or more cutting blades may be integrated along other surfaces of the tissue manipulation assembly as desired. Moreover, cutting blades may be integrated along the lower jaw, upper jaw, or both if so desired. Furthermore, the cutting blades may additionally be energized in further variations to facilitate severing the suture.

Although a number of illustrative variations are described above, it will be apparent to those skilled in the art that various changes and modifications may be made thereto without departing from the scope of the invention. Moreover, although specific configurations and applications may be shown, it is intended that the various features may be utilized in various combinations and in various types of procedures as practicable. It is intended in the appended claims to cover all such changes and modifications that fall within the true spirit and scope of the invention.

What is claimed is:

1. A method of deploying tissue anchors within a hollow body organ, comprising:
   endoluminally advancing a tissue grasping tool having a first jaw and a second jaw pivotably coupled to a distal end of an elongate member into the hollow body organ;
   clamping tissue within the hollow body organ with the first and second jaws of the tissue gasping tool;
   deploying at least one tissue anchor into or through the tissue through a deployment tube having a distal end that is attached to at least one of the first and second jaws of the tissue grasping tool; and
   severing a length of suture connecting the deployed at least one tissue anchor and depending from the tissue grasping tool with at least one cutting element disposed upon at least one of the first and second jaws of the tissue grasping tool.

2. The method of claim 1 wherein endoluminally advancing comprises advancing the tissue grasping tool transesophageally into a stomach.

3. The method of claim 1 wherein endoluminally advancing comprises advancing the tissue grasping tool along a flexible body with a steerable distal section transesophageally, wherein the flexible body is adapted to be rigidized to maintain an arbitrary shape.

4. The method of claim 1, wherein deploying at least one tissue anchor comprises:
   deploying a distal tissue anchor through a needle on a distal side of the clamped tissue;
   retracting the needle to a proximal side of the clamped tissue; and
   deploying a proximal tissue anchor through the needle on the proximal side of the clamped tissue.

5. The method of claim 4 further comprising cinching the proximal and distal tissue anchors to secure the clamped tissue prior to severing the suture.

6. The method of claim 5 wherein cinching the proximal and distal tissue anchors comprises advancing a pusher through the needle.

7. The method of claim 5, further comprising releasing the tissue from the tissue grasping tool after deploying the distal tissue anchor.

8. The method of claim 5, further comprising releasing the tissue from the tissue grasping tool prior to severing the length of suture.

9. The method of claim 1 further comprising engaging tissue within the hollow body organ with a tissue engagement device having a distal end effector adapted to reversibly engage tissue and further adapted to be positioned endoluminally within the hollow body organ adjacent to the tissue grasping tool.

10. The method of claim 1 wherein the tissue grasping tool comprises a first jaw member pivotably coupled to the distal end of the elongate member, a second jaw member pivotably coupled along the first jaw member, and a launch tube member adapted to urge the first and second jaw members between a low-profile delivery configuration and an expanded grasping configuration.

11. The method, of claim 10 wherein the at least one cutting element comprises a blade having a cutting edge.

12. The method of claim 10 wherein the at least one cutting element is positioned along the first jaw, the second jaw, or both the first and second jaws.

13. The method of claim 10 wherein the at least one cutting element is adapted to sever the length of suture depending from the launch tube member.

14. The method of claim 1, further comprising releasing the tissue from the tissue grasping tool after deploying the at least one tissue anchor.

15. The method of claim 1, further comprising releasing the tissue from the tissue grasping tool prior to severing, the length of suture.

\* \* \* \* \*